US007314910B2

(12) United States Patent
Boursaux-Eude et al.

(10) Patent No.: US 7,314,910 B2

(45) Date of Patent: Jan. 1, 2008

(54) **POLYPEPTIDES CONTAINING POLYMORPHISMS OF THE REPEATED REGIONS OF PERTACTIN IN *BORDETELLA PERTUSSIS, BORDETELLA PARAPERTUSSIS*, AND *BORDETELLA BRONCHISEPTICA*, THEIR USE IN DIAGNOSTICS, AND IN IMMUNOGENIC COMPOSITIONS**

(75) Inventors: Caroline Boursaux-Eude, Antony (FR); Nicole Guiso-Maclouf, Paris (FR)

(73) Assignee: Institut Pasteur, Paris (FR)

(*) Notice: Subject to any disclaimer, the term of this patent is extended or adjusted under 35 U.S.C. 154(b) by 89 days.

(21) Appl. No.: 11/088,785

(22) Filed: Mar. 25, 2005

(65) Prior Publication Data

US 2006/0008474 A1 Jan. 12, 2006

Related U.S. Application Data

(62) Division of application No. 09/855,754, filed on May 16, 2001, now Pat. No. 7,070,779.

(60) Provisional application No. 60/206,969, filed on May 25, 2000.

(51) Int. Cl.
*C07K 2/00* (2006.01)
*A61K 39/02* (2006.01)

(52) U.S. Cl. .................... 530/300; 424/184.1; 435/975

(58) Field of Classification Search ................ 530/300, 530/350; 424/190.1; 435/975
See application file for complete search history.

(56) References Cited

U.S. PATENT DOCUMENTS 6,387,377 B1 5/2002 Gueirard et al.
6,964,767 B2 11/2005 Guiso-Maclouf et al.

FOREIGN PATENT DOCUMENTS

WO WO 91/15571 10/1991
WO WO 92/11292 7/1993
WO WO 01/90143 A2 11/2001

OTHER PUBLICATIONS

International Search Report for Application No. PCT/EP 01/06457 (9 pages).

Boursaux-Eude, Caroline, et al., "Intranasal murine model of *Bordetella pertussis* infection: II. Sequence variation and protection induced by a tricomponent acellular vaccine," *Vaccine*, vol. 17, pp. 2651-2660 (1999).

Boursaux-Eude, Caroline, et al., "Polymorphism of repeated regions of pertactin in *Bordetella pertussis, Bordetella parapertussis*, and *Bordetella bronchiseptica*," *Infection and Immunity*, vol. 68, pp. 4815-4817 (2000).

Ellis, Ronald W., "New Technologies for Making Vaccines," *Vaccines*, WB Saunders Co., Philadelphia, pp. 568-575 (1988).

Khelef, Nadia, et al., "*Boardetella pertussis* and *Boretella parapertussis*: two immunologically distinct species," *Infect. Immun.*, 61, pp. 486-490 (1993).

Li, J., et al., "Cloning, nucleotide sequence and heterologous expression of the protective outer-membrane protein P. 68 pertactin from *Bordetella bronchiseptica*," *J. Gen. Microbiol.*, 138, pp. 1697-1705 (1992).

Li, L.J., et. al., "P.70 pertactine, an outer-membrane protein from *Bordetella parapertussis*: cloning nucleotide sequence and surface expression in *Escherichia coli*," *Mol. Microbiol.*, 5, pp. 409-417 (1991).

Mooi, Frits R., et al., "Polymorphism in the *Bordetella pertussis* virulence factors P. 69/Pertactin and Pertussis toxin in the Netherlands: Temporal trends and evidence for vaccine-driven evolution," *infection and Immunity*, vol. 66, pp. 670-675 (1998).

Pagliaccia, Cristina, et al., "Pertactin antigens extracted from *Bordetella pertussis* and *Bordetella bronchiseptica* differ in the isoelectric point," *Arch. Microbiol.*, vol. 168, pp. 437-440 (1997).

Register, Karen B., "Novel genetic and phenotypic heterogeneity in *Bordetella bronchiseptica* pertactin," *Infection and Immunity*, vol. 69, pp. 1917-1921 (2001).

*Primary Examiner*—Mark Navarro
(74) *Attorney, Agent, or Firm*—Finnegan, Henderson, Farabow, Garrett & Dunner, L.L.P.

(57) ABSTRACT

Pertactin (PRN) is an outer membrane protein expressed by *Bordetella pertussis, Bordetella parapertussis*, and *Bordetella bronchiseptica*, which induces protective immunity to *Bordetella* infections. The immunodominant and immunoprotective epitopes of pertactin include two repeated regions, I and II. Comparison of these two repeated regions showed the pertactin of *B. parapertussis* is invariant, whereas the pertactin of *B. pertussis* varies mostly in region I and *B. bronchiseptica* varies in both the repeated regions I and II. Compositions containing pertactins and pertactin fragments containing variant sequences in these regions are useful as immunogenic compositions.

3 Claims, 1 Drawing Sheet

Fig. 1a: The two regions of repeats in *Bordetella bronchiseptica* pertactin

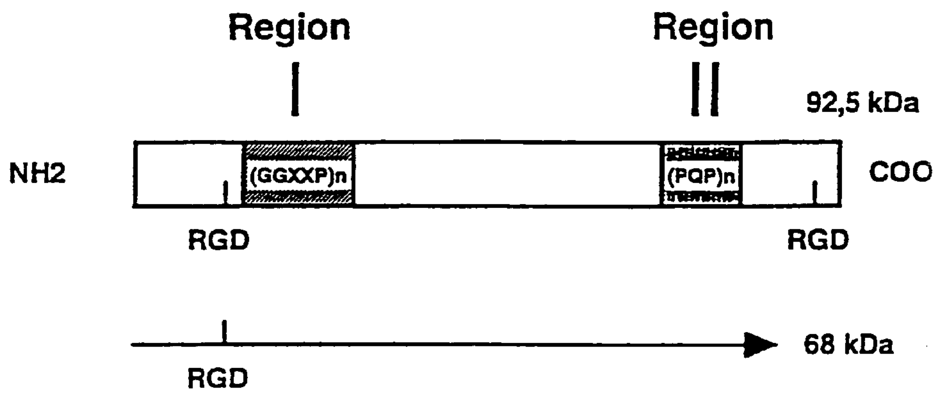

Fig. 1b: Multiple alignment of *B. bronchiseptica* pertactin in region I

```
I-1     QRATIRRGDAPAGGAVPGGAVPGGAVPG---------------GFGPLLDGWYGVDVSDSTVDLAQ
I-2     QRATIRRGDAPAGGAVPG-----GAVPG---------------GFGPLLDGWYGVDVSDSTVDLAQ
I-3     QRATIRRGDAPAGGGVPG-----GAVPG-----GFDPGGFGPGGFGPVLDGWYGVDVSGSTVELAQ
prn1    QRATIRRGDAPAGGAVPG-----GAVPG-----GAVPGGFGPGGFGPVLDGWYGVDVSGSSVELAQ
prn2    QRATIRRGDAPAGGAVPG-----GAVPGGFGPGGFGPGGFGPGGFGPVLDGWYGVDVSGSSVELAQ
prn3    QRATIRRGDAPAGGAVPG-----GAVPG-----GFGPGGFGPGGFGPVLDGWYGVDVSGSSVELAQ
prn4    QRATIRRGDAPAGGAVPG-----GAVPG----------GFGPGGFGPVLDGWYGVDVSGSSVELAQ

        ************** ***     *****               ****.********** *.*.***
```

Fig. 1c: Multiple alignment of *B. bronchiseptica* pertactin in region II

```
II-1    GAKAPPAPKPAPQPGPQPGP-----------QPPQPPQP-PQRQP--EAPAPQPPAGRELSAA
II-2    GAKAPPAPKPAPQPGPQPGPQPP--------QPPQPPQP-PQRQP--EAPAPQPPAGRELSAA
II-3    GAKAPPAPKPAPQPGPQPGPQPGPQPGPQPPQPPQPPQP-PQRQP--EAPAPQPPAGRELSAA
II-4    GAKAPPAPKPAPQPGPQPGPQPGP-------QPPQPPQP-PQRQP--EAPAPQPPAGRELSAA
II-5    GAKAPPAPKPAPQPGPQPGPQPGPQP----PQPPQPPQP-PQRQP--EAPAPQPPAGRELSAA
II-6    GAKAPPAPKPAPQPGPQPGPQPPQPP--QPPQPPQPPQP-PQRQP--EAPAPQPPAGRELSAA
II-7    GAKAPPAPKPAPQPGPQP-P-----------QPPQPPQP-PQRQP--EAPAPQPPAGRELSAA
II-8    GAKVPPAPKPAPQPGPQP-PQPP--------QPPQPPQPQPQPQP--EAPAPQPPAGRELSAA
II-9    GAKVPPAPKPAPQPGPQP-PQPP--------QPPQPPQPQPQPQPQPEAPAPQPPAGRELSAA
prn1    GAKAPPAPKPAPQPGPQP---------------PQPPQP----QP--EAPAPQPPAGRELSAA
prn6    GAKAPPAPKPAPQPGPQP------------------PQP----QP--EAPAPQPPAGRELSAA

        *** ***************                 ***    **  ****************
```

POLYPEPTIDES CONTAINING POLYMORPHISMS OF THE REPEATED REGIONS OF PERTACTIN IN *BORDETELLA PERTUSSIS, BORDETELLA PARAPERTUSSIS*, AND *BORDETELLA BRONCHISEPTICA*, THEIR USE IN DIAGNOSTICS, AND IN IMMUNOGENIC COMPOSITIONS

CROSS-REFERENCE TO RELATED APPLICATIONS

This application is a division of U.S. application Ser. No. 09/855,754, filed May 16, 2001, now U.S. Pat. No. 7,070,779, which is based on and claims the benefit of U.S. Provisional Application Ser. No. 60/206,969, filed May 25, 2000. The entire disclosure of both are relied upon and incorporated by reference herein.

BACKGROUND OF THE INVENTION

This invention relates to proteins and polypeptides of the *Bordetella* outer membrane protein called pertactin and the polynucleotides that encode them. This invention also relates to the use of these proteins and polypeptides in immunogenic compositions, diagnostic methods, and diagnostic kits.

The genus *Bordetella* includes seven species. The most studied species are *B. pertussis, B. parapertussis*, and *B. bronchiseptica. B. pertussis* is responsible for respiratory infections only in humans. *B. parapertussis* causes infections in humans and sheep, and *B. bronchiseptica* infects many animal species, including humans.

These pathogens produce an array of virulence factors, the synthesis of which is regulated by the two-component, bvg AS (2, 21) system. These factors include toxins, such as pertussis toxin, which is the only toxin specific to *B. pertussis*, tracheal cytotoxin, adenylate cyclase-hemolysin, and adhesins, such as filamentous hemagglutinin, fimbriae, and pertactin (PRN).

PRN is an outer membrane protein with an apparent molecular weight of 69 kDa in *B. pertussis,* 70 kDa in *B. parapertussis*, and 68 kDa in *B. bronchiseptica* (5, 14, 15). The precursors of PRN are 91.5 kDa, 93 kDa, and 92.5 kDa in size, respectively. In *B. pertussis*, PRN has been demonstrated to be an agglutinogen (4), promoting attachment to certain eukaryotic cells via an Arg-Gly-Asp (RGD) motif (13).

Antibodies specific for the *B. bronchiseptica* PRN are detected at high titer in immunized piglets, whereas few if any of these antibodies are detected in unprotected animals (19). Synthesis of the PRN by *B. bronchiseptica* correlates with protection (16). The immunization of mice or piglets with preparations of the PRN induces protective immunity against *B. bronchiseptica* infection (12, 19) and passively administered monoclonal antibodies prevent the death of animals challenged with *B. bronchiseptica* (16). *B. pertussis* PRN has also been shown to induce protective immunity to intracerebral, aerosol and intranasal challenges with *B. pertussis* in mice (11, 18, 20).

PRN is, therefore, now included in some acellular pertussis vaccines (i.e. vaccines composed of purified bacterial proteins) (9). However, the PRN proteins of these three species, although clearly related, have different immunogenic properties. For example, preparations of *B. pertussis* PRN protect mice against intranasal *B. pertussis* challenge but not against intranasal *B. parapertussis* challenge (11).

They also protect mice against intracerebral *B. pertussis* challenge, whereas the *B. bronchiseptica* PRN protein does not (18).

Comparison of the deduced amino acids of the three proteins, *B. pertussis*-PRN, *B. parapertussis*-PRN, and *B. bronchiseptica*-PRN, reveals a high degree of similarity, with the *B. bronchiseptica* and *B. parapertussis* proteins being more similar to each other than to the *B. pertussis* PRN protein (5, 14, 15).

The sequences of the three proteins differ in the number of repeats in regions I and II (FIG. 1*a*). Using monoclonal antibodies, Charles et al., identified and characterized a protective immunodominant epitope of the P.69-PRN protein (6). This epitope spans the (Pro-Gln-Pro)5 repeat sequences located in region II. Differences in this region may account for the observation that sera from piglets that recognize *B. bronchiseptica* PRN do not react with *B. pertussis* PRN despite the high degree of similarity between these proteins (12) and for the lack of cross protection provided by the three proteins (11, 18, 20).

It has recently been shown that the PRN produced by clinical isolates of *B. pertussis* varies. Sequences of the prn gene of various clinical isolates revealed three major types of PRN variant (17). It has been suggested that epidemics in the Netherlands result from changes in the sequences of the genes encoding PRN and PT because the proteins present in the clinical isolates currently in circulation differ in sequence from those observed by the vaccinal strains used in this country (17).

For PRN of *B. pertussis*, all the observed amino acid differences are located in region I. The allelic prn types A=1 and C=3 are very similar, differing by only two amino acids, whereas type B=2 is quite different, having a five-amino acid insertion in the same region (17).

Only one type was found to differ in region II. This type (A*=6) is produced by the *B. pertussis* WHO reference strain 18323 and one French clinical isolate (3). It does not, however, seem to be common because it has been detected in only one clinical isolate (3). The production by this *B. pertussis* strain of this unusual type of PRN reflects the many common properties shared with the *B. parapertussis* and *B. bronchiseptica* species. No differences were found in the phenotype and behavior in the animal model of *B. pertussis* clinical isolates with different PRN (3).

There is a need in the art for compositions containing proteins and polypeptides of *Bordetella* pertactins that can be used in immunogenic compositions to protect against *Bordetella* infection and to treat subjects infected with *Bordetella*. Ideally, the proteins, polypeptides, and the polynucleotides that encode them would also be useful in diagnosing *Bordetella* infection and in kits for the diagnosis of such infection.

SUMMARY OF THE INVENTION

This invention aids in fulfilling these needs in the art. In one embodiment, this invention provides an immunogenic composition comprising a mixture of pertactins of *Bordetella* species, wherein said composition comprises: (a) pertactin of *Bordetella parapertussis*, and (b) pertactin of *Bordetella bronchiseptica*, in amounts sufficient to induce a humoral or cellular immune response against *Bordetella parapertussis* and *Bordetella bronchiseptica* in an animal to which the immunogenic composition is administered. The immunogenic composition can also comprise pertactin of *Bordetella pertussis* in an amount sufficient to induce a humoral or cellular immune response against *Bordetella pertussis* in an animal to which the immunogenic composition is administered.

In another embodiment, the immunogenic composition of the invention comprises a mixture of pertactins of *Bordetella* species or fragments thereof. Specifically, the mixture comprises a mixture of *Bordetella bronchiseptica* pertactin variants wherein each *Bordetella bronchiseptica* pertactin variant comprises 6, 7, 8, or 9 repeating PQP amino acid sequences in Region II thereof. The *Bordetella bronchiseptica* pertactin variants are present in amounts sufficient to induce a humoral or cellular immune response against *Bordetella bronchiseptica* in an animal to which the immunogenic composition is administered. This immunogenic composition can also comprise pertactins of *Bordetella parapertussis, Bordetella pertussis*, or mixtures thereof, in amounts sufficient to induce a humoral or cellular immune response against *Bordetella parapertussis* or *Bordetella pertussis* in an animal to which the immunogenic composition is administered.

In a further embodiment of the invention, the immunogenic composition comprises a mixture of pertactins of *Bordetella* species or fragments thereof, wherein mixture comprises a mixture of *Bordetella bronchiseptica* pertactin variants, wherein each *Bordetella bronchiseptica* pertactin variant comprises 1, 2, or 3 repeating GGXXP amino acid sequences in Region I thereof. The *Bordetella bronchiseptica* pertactin variants are present in amounts sufficient to induce a humoral or cellular immune response against *Bordetella bronchiseptica* in an animal to which the immunogenic composition is administered. This immunogenic composition can also comprise pertactins of *Bordetella parapertussis, Bordetella pertussis*, or mixtures thereof, in amounts sufficient to induce a humoral or cellular immune response against *Bordetella parapertussis* or *Bordetella pertussis* in an animal to which the immunogenic composition is administered.

The compositions of the invention can comprise a mixture of fragments of the pertactins of *Bordetella* species. The immunogenic compositions can also comprise at least one polypeptide of the invention in an amount sufficient to induce an immunogenic or protective response in vivo, and a pharmaceutically acceptable carrier therefor. In addition, the immunogenic composition can comprise a neutralizing amount of at least one polypeptide of the invention.

A preferred immunogenic composition of this invention comprises a mixture of pertactins of *Bordetella bronchiseptica* species or fragments thereof, wherein the pertactins or fragments thereof comprise a mixture of *Bordetella bronchiseptica* pertactin variants in which at least one of the *Bordetella bronchiseptica* pertactin variants comprises Region II of pertactin of *Bordetella bronchiseptica* having 6, 7, 8, or 9 repeating PQP amino acid sequences in Region II thereof, and at least another of the *Bordetella bronchiseptica* pertactin variants comprises Region I of pertactin of *Bordetella bronchiseptica* having 1, 2, or 3 repeating GGXXP amino acid sequences in Region I thereof.

In another preferred embodiment, the immunogenic composition of the invention consists essentially of (A) a polypeptide comprising Region I and Region II, or one polypeptide comprising Region I and one polypeptide comprising Region II, of a pertactin of *Bordetella pertussis*; (B) a polypeptide comprising Region I and Region II, or one polypeptide comprising Region I and one polypeptide comprising Region II, of a pertactin of *Bordetella parapertussis*; (C) a polypeptide comprising Region I and Region II, or one polypeptide comprising Region I and one polypeptide comprising Region II, of a pertactin of *Bordetella bronchiseptica* strain 9.73 and a polypeptide comprising Region I and Region II, or one polypeptide comprising Region I and one polypeptide comprising Region II, of a pertactin of *Bordetella bronchiseptica* of strain SEI.

This invention also provides polynucleotides encoding the proteins and polypeptides of the invention, as well as antibodies that recognize the proteins and polypeptides. Also provided is a DNA chip, wherein said chip comprises at least one polynucleotide according to the invention or fragment thereof or a microarray comprising microbeads, wherein the microbeads each bears multiple copies of a polynucleotide, wherein the polynucleotide encodes a polypeptide consisting of, comprising, or comprising a fragment of a sequence selected from the group consisting of: SEQ ID NO:7, SEQ ID NO:8, SEQ ID NO:9, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22 and wherein the polynucleotide or fragment thereof is different from one bead to another.

The antibodies can be monoclonal or polyclonal antibodies. Monoclonal antibodies can be used for treating *Bordetella* infections. Also provided are immunological complexes comprising a protein or polypeptide of the invention and an antibody that specifically recognizes the protein or polypeptide.

Further, this invention provides a method for detecting infection by *Bordetella*. The method comprises providing a composition comprising a biological material suspected of being infected with *Bordetella* and assaying for the presence of a protein or polypeptide of the invention. The polypeptide can be assayed, for example, by electrophoresis or by immunoassay with antibodies that are immunologically reactive with the polypeptide.

The method can also comprise contacting the antigen with a biological fluid for a time and under conditions sufficient for the antigen and antibodies in the biological fluid to form an antigen-antibody complex, and detecting the formation of the complex. The method optionally can include measuring the formation of the antigen-antibody complex. In preferred embodiments, formation of antigen-antibody complex is detected by immunoassay based on Western blot technique, ELISA, indirect immunofluorescence assay, or immunoprecipitation assay.

Further, this invention provides a diagnostic kit for the detection of the presence or absence of antibodies, which bind a protein or polypeptide of the invention or mixtures thereof. The kit can comprise an antigen comprising the protein or polypeptide, or mixtures of the proteins and polypeptides, and means for detecting the formation of immune complexes between the antigen and antibodies. The means are present in an amount sufficient to perform the detection.

Another method of the invention for detecting the presence or absence of *Bordetella* comprises (1) contacting a sample suspected of containing genetic material of *Bordetella* with at least one nucleotide probe, and (2) detecting hybridization between the nucleotide probe and the genetic material in the sample. The nucleotide probe is complementary to a polynucleotide sequence of the invention.

BRIEF DESCRIPTION OF THE DRAWINGS

This invention will be described in greater detail with reference to the drawings in which:

FIG. 1*a* is a map of the two regions of repeats, Region I and Region II, in the pertactin outer membrane protein of *Bordetella bronchiseptica*.

FIG. 1b is an alignment of Region I of the pertactin outer membrane protein of different strains of B. bronchiseptica.

FIG. 1c is an alignment of Region II of the pertactin outer membrane protein of different strains of B. bronchiseptica.

DETAILED DESCRIPTION OF THE INVENTION

It has been demonstrated previously that species-specific members of the pertactin family are outer-membrane proteins (OMPs). In B. bronchiseptica, pertactin is the product of the pm gene and is represented as a protein with an $M_r$ of 68 kDa (P.68), in B. pertussis as a protein with an $M_r$ of 69 kDa (P.69), and in B. parapertussis as a protein with an $M_r$ of 70 kDa (P.70). The nucleotide sequences of the pertactins of these three species are included in the accompanying Sequence Listing as SEQ ID NO:1, SEQ ID NO:2, and SEQ ID NO:3, respectively. The corresponding amino acid sequences encoded by these nucleotide sequences are included in the sequence listing as SEQ ID NO:4, SEQ ID NO:5, and SEQ ID NO:6, respectively.

A comparison of the deduced protein sequences for the P.68, P.69. and P.70 proteins demonstrates the high degree of homology between the proteins. A comparison between the P.68 and P.70 proteins shows only 17 amino acid differences, while a similar comparison between P.68 and P.69 shows 80 differences, and 79 differences between P.69 and P.70. The majority of amino acid differences between the three deduced protein sequences occur in the number of repeat units in the two families of repeat sequences present in all three proteins. P.68 has three copies of the Gly-Gly-Xaa-Xaa-Pro repeat (i.e., GGXXP in FIG. 1b), while P.70 has four and P.69 five. Similarly, P.68 has seven Pro-Gln-Pro repeats (i.e., PQP in FIG. 1c), P.70 has nine and P.69 has five.

It has recently been shown that the PRN produced by clinical isolates of B. pertussis varies. Sequences of the prn gene of various clinical isolates revealed three major types of PRN variant. It has been suggested that epidemics in the Netherlands result from changes in the sequences of the genes encoding PRN and PT because the proteins present in the clinical isolates currently in circulation differ in sequence from those observed by the vaccinal strains used in this country.

An aim of the searches, which led to the present invention, was to analyze whether the PRN polymorphism observed in B. pertussis species also occurs in B. parapertussis and B. bronchiseptica. The two repeated regions of the prn genes of 10 B. parapertussis isolates of human origin and of 40 B. bronchiseptica isolates of animal or human origin were sequenced and compared. (FIG. 1a).

Table I contains a list of the isolates and corresponding pertactin types used in this invention.

TABLE I

| Bordetella Species | Representative isolate | PRN regions I and II types/ Number of isolates | Accession number,* region I, region II |
|---|---|---|---|
| BB | 9.73H+ | I-1, II-3/3 | AJ250076, AJ250077 |
| BB | LAPR | I-2, II-3/8 | AJ250078, AJ250079 |
| BB | 5 | 1-2, II-4/8 | AJ250080, AJ250081 |
| BB | 335 | I-2, II-1/3 | AJ250082, AJ250083 |

TABLE I-continued

| BB | CVGEO | I-2, II-5/6 | AJ250084, AJ250085 |
|---|---|---|---|
| BB | BBCH | I-2, II-6/4 | AJ250086, AJ250087 |
| BB | DEL | I-1, II-2/5 | AJ250088, AJ25089 |
| BB | CAT1 | I-1, II-7/1 | AJ250090, AJ250091 |
| BB | 286 | I-3, II-8/1 | AJ250093, AJ250092 |
| BB | SEI | I-3, II-9/1 | AJ250094, AJ250095 |
| BPP | 63.2 | I-1, II-2/10 | Identical to P24328 |

| Species | Strain | PRN type | Accession number |
|---|---|---|---|
| BPP | CN2591 | I-1, II-2 | P24328 |
| BB | CN7531 | I-2, II-4 | Q03035 |

| Species | Strain or isolate | Allelic prn type | Accession number |
|---|---|---|---|
| BP | Tohama | prn1 | AJ006158 |
| BP | 18323 | prn6 | AJ006152 |
| BP | Hav | prn2 | AJ007361 |
| BP | Fr287 | prn3 | AJ006156 |

BB: B. bronchiseptica;
BP: B. pertussis;
BPP: B. parapertussis
*EMBL Bank.

In carrying out this invention, DNA was extracted, amplified by PCR, and sequenced, as previously described (3). Amplified PCR products were purified and sequenced by the ESGS company (ESGS, Cybergene group, Evry, France). Deduced amino acid sequences were analyzed with GCG software (Wisconsin Package Version 9.1, Genetics Computer Group, Madison, Wis., USA). The deduced amino acid sequences of regions I and II were compared and multiple alignments of the amino acid sequences were created with the CLUSTAL W program of GCG (10), for each region (FIG. 1b,c).

No difference was found between the sequences of regions I and II of the PRN produced by the 10 B. parapertussis isolates and the published sequence (15). However, three different types were found among the 40 B. bronchiseptica prn genes analyzed with differences in the number of repeats (1 to 3) in region I (FIG. 1b). The largest group corresponded to sequences with three copies of the repeated sequence, identical to the sequence previously reported (14). No correlation was found between the pattern of variation and the origin of the isolate.

A higher degree of variability was observed in the second repeated region of the B. bronchiseptica PRN (FIG. 1c). Nine variants were observed. Among these nine variants the number of repeats is from 6 to 9.

No B. bronchiseptica variants presented the same pattern as the B. pertussis variants. Furthermore, no unique association between one type of region I and one type of region II was observed. No observation was made in any of the three species of a pattern similar to those of the 18323 strain and the CZ isolate (3), which are considered to be intermediate between B. pertussis, B. bronchiseptica, and parapertussis. These data are consistent with B. parapertussis and B. bronchiseptica prn genes being more similar to each other than to the B. pertussis prn gene (1). No host specificity was observed with respect to PRN type.

It has been shown that region II plays an important role in the induction of protective immunity (6). The lack of cross-protection between PRN from B. pertussis, B. parapertussis, and *B. bronchiseptica* PRN is consistent with this, because the major differences between these proteins occur in this region. No variation in this region was observed for the PRN produced by *B. pertussis* isolates. These data suggest that thirty years of vaccination may have induced variation in one immunodominant repeat region, but not in the region most involved in the induction of protective immunity. Variation in *B. pertussis* PRN region II may indicate a decrease in *B. pertussis* vaccine efficacy.

In contrast, analysis of the PRN of *B. bronchiseptica* showed polymorphism in both regions. This may account for the inability of *B. bronchiseptica* vaccines to induce long-lasting protection. This polymorphism may also be linked to the ability of *B. bronchiseptica* to induce chronic infections (7, 8, 22). It may provide a means for this bacterium to escape host immune responses.

This invention, which resulted from these experiments and observations, thus involves compositions containing certain *Bordetella* pertactins and fragments thereof. These pertactins and pertactin fragments, as well as the polynucleotides that encode them, are useful in immunogenic compositions and in diagnostic applications.

In particular, this invention is the result of the discovery that there are different species of the full length pertactin of *Bordetella bronchiseptica*, namely, species containing 6, 7, 8, or 9 repeating PQP amino acid sequences in Region II thereof, and species of full length pertactin of *B. bronchiseptica* containing 1, 2, or 3 repeating GGXXP amino acid sequences in Region I thereof, where XX can be FD, FG, or AV. These full length pertactins and mixtures of these pertactins in any combination of the repeating sequences are thus provided by this invention.

As used herein, the expression "pertactin of *Bordetella bronchiseptica*" means an outer membrane protein of *Bordetella bronchiseptica*, which is a virulence factor, and which has an apparent molecular weight of about 68 kDa, and which contains the two regions of *Bordetella bronchiseptica* pertactin known as Region I and Region II. Region I and Region II of the pertactins of different *Bordetella* strains are identified in brackets in SEQ ID NOS: 1 to 6. It will be understood that the pertactins of different isolates of *Bordetella bronchiseptica* may have amino acid sequences that differ from each other, for example, in Region I, Region II, or both Region I and Region II, as well as in other regions.

As used herein the expression "*Bordetella bronchiseptica* pertactin variants" means pertactins of *Bordetella bronchiseptica*, or fragments of pertactins of *Bordetella bronchiseptica* containing at least Region I, Region II, or both Region I and Region II, in which the pertactins of *Bordetella bronchiseptica* or the fragments thereof differ from each other in at least Region I, Region II, or both Region I and Region II, in their respective amino acid sequences. The following unique *Bordetella bronchiseptica* pertactin variants have been discovered and constitute part of this invention.

As used herein the expressions "*Bordetella bronchiseptica* pertactin fragments", "*Bordetella parapertussis* pertactin fragments", and "*Bordetella pertussis* pertactin fragments" refer to polypeptides that are portions of full length pertactin proteins and are capable of inducing a humoral or immune response against *Bordetella* infections.

*B. bronchiseptica* pertactin - region I

```
I-1  QRATIRRGDAPAGGAVPGGAVPGGAVPG---------------GFGPLLDGWYGVDVSDSTVDLAQ  (SEQ ID NO: 7)

I-2  QRATIRRGDAPAGGAVPG-----GAVPG---------------GFGPLLDGWYGVDVSDSTVDLAQ  (SEQ ID NO: 8)

I-3  QRATIRRGDAPAGGGVPG-----GAVPG-----GFDPGGFGPGGFGPVLDGWYGVDVSGSTVELAQ  (SEQ ID NO: 9)

prn1 QRATIRRGDAPAGGAVPG-----GAVPG-----GAVPGGFGPGGFGPVLDGWYGVDVSGSSVELAQ  (SEQ ID NO: 10)

prn2 QP.ATIRRGDAPAGGAVPG----GAVPGGFGPGGFGPGGFGPGGFGPVLDGWYGVDVSGSSVELAQ  (SEQ ID NO: 11)

prn3 QRATIRRGDAPAGGAVPG-----GAVPG-----GFGPGGFGPGGFGPVLDGWYGVDVSGSSVELAQ  (SEQ ID NO: 12)

prn4 QRATIRRGDAPAGGAVPG-----GAVPG----------GFGPGGFGPVLDGWYGVDVSGSSVELAQ  (SEQ ID NO: 13)

**************.***     *****           ****.**********.*:*:***
```

*B. bronchiseptica* pertactin - region II

```
II-1 GAKAPPAPKPAPQPGPQPGP-----------QPPQPPQP-PQRQP--EAPAPQPPAGRELSAA     (SEQ ID NO: 14)

II-2 GAKAPPAPKPAPQPGPQPGPQPP--------QPPQPPQP-PQRQP--EAPAPQPPAGRELSAA     (SEQ ID NO: 15)

II-3 GAKAPPAPKPAPQPGPQPGPQPGPQPGP---QPPQPPQP-PQRQP--EAPAPQPPAGRELSAA     (SEQ ID NO: 16)

II-4 GAKAPPAPKPAPQPGPQPGPQPGP-------QPPQPPQP-PQRQP--EAPAPQPPAGRELSAA     (SEQ ID NO: 17)

II-5 GAKAPPAPKPAPQPGPQPGPQPGPQP----PQPPQPPQP-PQRQP--EAPAPQPPAGRELSAA     (SEQ ID NO: 18)

II-6 GAKAPPAPKPAPQPGPQPGPQPPQPP--QPPQPPQPPQP-PQRQP--EAPAPQPPAGRELSAA     (SEQ ID NO: 19)

II-7 GAKAPPAPKPAPQPGPQP-P-----------QPPQPPQP-PQRQP--EAPAPQPPAGRELSAA     (SEQ ID NO: 20)

II-8 GAKVPPAPKPAPQPGPQP-PQPP--------QPPQPPQPQPQPQP--EAPAPQPPAGRELSAA     (SEQ ID NO: 21)

II-9 GAKVPPAPKPAPQPGPQP-PQPP--------QPPQPPQPQPQPQPQPEAPAPQPPAGRELSAA     (SEQ ID NO: 22)

prn1 GAKAPPAPKPAPQPGPQP---------------PQPPQP----QP--EAPAPQPPAGRELSAA     (SEQ ID NO: 23)

prn6 GAKAPPAPKPAPQPGPQP------------------PQP----QP--EAPAPQPPAGRELSAA     (SEQ ID NO: 24)
```

In specific embodiments, this invention includes a polypeptide comprising a sequence or a fragment of a sequence selected from the group consisting of SEQ ID NO:7, SEQ ID NO:8, SEQ ID NO:9, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22. The polypeptide can consist of the amino acids in SEQ ID NO:7, SEQ ID NO:8, SEQ ID NO:9, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22 or fragments thereof. The invention also includes polynucleotides encoding one of these polypeptides and a purified DNA or RNA sequence that hybridizes under moderate or high stringency conditions to the polynucleotides or at least to 15 nucleotides thereof.

As used herein, the expression "mixture of *Bordetella bronchiseptica* pertactin variants" means two or more *Bordetella bronchiseptica* pertactin variants in admixture in solid, liquid, emulsion, or suspension form. At least two of the *Bordetella bronchiseptica* pertactin variants in the mixture will, of course, differ from each other in at least Region I, Region II, or both Region I and Region II, in their respective amino acid sequences.

It will be immediately apparent that this invention provides polypeptide fragments of the pertactin of *B. bronchiseptica*, where the fragments comprise 6, 7, 8, or 9 repeating PQP amino acid sequences in Region II thereof or 1, 2, or 3 repeating GGXXP amino acid sequences in Region I thereof. Mixtures of these polypeptide fragments in any combination of the repeating sequences are also within the scope of this invention.

When a polypeptide fragment of the invention comprises only Region I of a pertactin of *B. bronchiseptica*, the polypeptide fragment typically contains at least about 46 to about 56 amino acids, which includes the Region I repeat sequences. When the polypeptide fragment of the invention comprises only Region II, the polypeptide fragment typically contains at least about 48 to about 60 amino acids, which includes the Region II repeat sequences. When the polypeptide fragment of the invention comprises both Region I and Region II of *B. bronchiseptica*, the fragment typically contains at least about 906 to about 928 amino acids, which includes the repeat sequences of Regions I and II.

Thus, in one illustrative embodiment, this invention provides a composition comprising a mixture of *Bordetella bronchiseptica* pertactin variants, wherein each *Bordetella bronchiseptica* pertactin variant comprises Region II of pertactin of *Bordetella bronchiseptica*, and further wherein each *Bordetella bronchiseptica* pertactin variant comprises 6, 7, 8, or 9 repeating PQP amino acid sequences in Region II thereof, and the *Bordetella bronchiseptica* pertactin variants differ in the number of the repeating PQP amino acid sequences contained therein. The composition can also comprise pertactins of *Bordetella parapertussis, Bordetella pertussis*, or mixtures thereof. The polypeptide can be a full length pertactin or a fragment thereof.

In another embodiment, this invention provides a composition comprising a mixture of *Bordetella bronchiseptica* pertactin variants, wherein each *Bordetella bronchiseptica* pertactin variant comprises Region I of a pertactin of *Bordetella bronchiseptica*, and further wherein each *Bordetella bronchiseptica* pertactin variant comprises 1, 2, or 3 repeating GGXXP amino acid sequences in Region I thereof, and the at least two of the *Bordetella bronchiseptica* pertactin variants differ in the number of the repeating GGXXP amino acid sequences contained therein. This composition can also comprise pertactins of *Bordetella parapertussis, Bordetella pertussis*, or mixtures thereof. The *Bordetella bronchiseptica* pertactin variants can be full length or a fragment.

In a further embodiment, the invention provides a composition comprising a mixture of *Bordetella bronchiseptica* pertactin variants, wherein one of the *Bordetella bronchiseptica* pertactin variants comprises Region II of pertactin of *Bordetella bronchiseptica* having 6, 7, 8, or 9 repeating PQP amino acid sequences in Region II thereof, and another of the *Bordetella bronchiseptica* pertactin variants comprises Region I of pertactin of *Bordetella bronchiseptica* having 1, 2, or 3 repeating GGXXP amino acid sequences in Region I thereof. This composition can also comprise pertactins of *Bordetella parapertussis, Bordetella pertussis*, or mixtures thereof. The *Bordetella bronchiseptica* pertactin variants can be full length or a fragment.

In a preferred embodiment, this invention provides a polypeptide comprising a sequence selected from the group consisting of SEQ ID NO: 7, SEQ ID NO: 8, or SEQ ID NO: 9.

In another preferred embodiment, this invention provides a polypeptide comprising a sequence selected from the group consisting of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or SEQ ID NO: 22.

The compositions according to the invention cause a humoral immune response and a cellular immune response. After infection with *B. bronchiseptica*, there is induction of a humoral immunity and of a cellular immunity, as in the case of a *B. pertussis* and *B. parapertussis* infection. Furthermore, after vaccination with compositions of this invention, there is induction of a humoral and cellular type immunity similar to that induced after infection or reinfection.

In one embodiment of the invention there is provided a vaccinating composition comprising as active principle an immunogenic composition of the invention, in combination with a pharmaceutically acceptable vehicle and, where appropriate, with an adjuvant.

Like the whooping cough vaccines currently available on the market, the immunogenic composition according to the invention may be combined with other vaccinating active principles, for example, those of the vaccine against diphtheria, polio, or diseases caused by *Haemophilus* or, generally speaking, with any immunogenic constituent, for example, a particular inactivated pathogenic agent or toxin.

A vaccinating composition according to the invention can be species-specific and consequently capable of inducing protection against *B. pertussis* or *B. parapertussis* or *B. bronchiseptica*. Alternatively, it can be a mixture comprising as active principle an immunogenic composition against *B. bronchiseptica*, as defined above, and an immunogenic composition against *B. parapertussis* and/or *B. pertussis.*

As a result of recent techniques in molecular biology, a number of factors involved in the virulence of *B. pertussis* have been characterized and the regulation of their expression understood. These factors may be classified in two categories, those participating in the infectious syndrome (adhesins) and those playing a part in the toxin-induced syndrome (toxins). The adhesins and toxins relating to *Bordetella* can be included in the compositions of this invention. Examples of the adhesins are:

filamentous hemagglutinin or FHA, considered to play a major part in the adhesion of the bacterium to the ciliated epithelium;

the two agglutinogens or AGGs of *B. pertussis*, which enable strains to be classified in serotypes; and pertussis toxin or PTX, a secreted type A-B toxin which, besides its cytopathogenic effects, participates in adhesion via its B subunit.

Examples of the toxins for use in the invention are:

pertussis toxin or PTX, which is secreted;

dermonecrotic toxin or DNT, which function has not yet been well characterized, and tracheal cytotoxin or TCT, a secreted small glycoprotein of the muramyl peptide family, derived from the peptidoglycan of the bacterium, which appear to act in concert to destroy the ciliated cells of the host's respiratory apparatus;

adenylate cyclase-hemolysin or Ac-Hly, a bifunctional protein possessing adenylate cyclase activity and hemolytic activity, which has been found to belong to the family of toxins termed "RTX" for "repeats in toxins".

Similarly, the factors involved in the virulence of *B. parapertussis* and *B. bronchiseptica* have been identified and can be included in the compositions of the invention.

The published results show that the acellular vaccines tested, monovalent (PTX), bivalent (PTX, FHA), trivalent (PTX, FHA, PRN), or pentavalent (PTX, FHA, PRN, AGG2, AGG3) induce very few side effects, are all immunogenic and all have an efficacy against the disease (according to WHO definition) which is greater than or equal to 70%. The compositions of the invention can be included in these vaccines and other acellular vaccines. For example, the immunogenic composition can further comprise at least one adhesin of *Bordetella* selected from the group consisting of FHA, AGG2, AGG3, and/or at least one toxin of *Bordetella* selected from the group consisting of PTX, DNT, TCT, and Ac-Hly.

The proteins, polypeptides, and compositions of this invention can be in purified form. The term "purified" as used herein, means that the pertactins and fragments thereof are essentially free of association with other proteins or polypeptides, for example, as a purification product of recombinant host cell culture or as a purified product from a non-recombinant source. The term "substantially purified" as used herein, refers to a mixture that contains pertactins or fragments thereof and is essentially free of association with other proteins or polypeptides, but for the presence of known proteins that can be removed using a specific antibody, and which substantially purified pertactin polypeptides can be used as antigens.

Within an aspect of the invention, the pertactin and fragments thereof can be utilized to prepare antibodies that specifically bind to pertactin polypeptides. The term "antibodies" is meant to include polyclonal antibodies, monoclonal antibodies, fragments thereof, such as F(ab')2 and Fab fragments, as well as any recombinantly produced binding partners. Antibodies are defined to be specifically binding if they bind pertactins and fragments thereof with a $K_a$ of greater than or equal to about $10^7$ $M^{-1}$. Affinities of binding partners or antibodies can be readily determined using conventional techniques, for example, those described by Scatchard et al., *Ann. N.Y Acad Sci.*, 51:660 (1949). Polyclonal antibodies can be readily generated from a variety of sources, for example, horses, cows, goats, sheep, dogs, chickens, rabbits, mice, or rats, using procedures that are well known in the art.

The invention further encompasses isolated fragments and oligonucleotides derived from the nucleotide sequence of the pertactins *B. bronchiseptica, B. pertussis* and *B. parapertussis* (SEQ ID NO: 1, SEQ ID NO:2, and SEQ ID NO:3) encoding 6, 7, 8, or 9 repeating PQP amino acid sequences in Region II thereof, and/or 1, 2, or 3 repeating GGXXP amino acid sequences in Region I thereof. The invention also encompasses polypeptides encoded by these fragments and oligonucleotides. Mixtures can comprise nucleotide sequences containing repeating sequences in which each entity in the mixture is independently selected from the polynucleotides of the invention.

Nucleic acid sequences within the scope of the invention include isolated DNA and RNA sequences that hybridize to the native pertactin nucleic acids disclosed herein under conditions of moderate or severe stringency, and which encode pertactin polypeptides. As used herein, conditions of moderate stringency, as known to those having ordinary skill in the art, and as defined by Sambrook et al. *Molecular Cloning: A Laboratory Manual*, 2 ed. Vol. 1, pp. 1.101-104, Cold Spring Harbor Laboratory Press, (1989), include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of about 60° C., 0.5×SSC, 0.1% SDS. Conditions of high stringency are defined as hybridization conditions as above, and with washing at 68° C., 0.2×SSC, 0.1% SDS. The skilled artisan will recognize that the temperature and wash solution salt concentration can be adjusted as necessary according to factors such as the length of the probe.

Due to the known degeneracy of the genetic code, wherein more than one codon can encode the same amino acid, a DNA sequence can vary and still encode a pertactin polypeptide having the amino acid sequence of SEQ ID NO:7 through SEQ ID NO:24. Such variant DNA sequences can result from silent mutations (e.g., occurring during PCR amplification), or can be the product of deliberate mutagenesis of a native sequence.

The invention thus provides equivalent isolated DNA sequences, encoding pertactin polypeptides, selected from: (a) DNA derived from the coding region of a native pertactin gene; (b) cDNA comprising the nucleotide sequence of SEQ ID NO:7 through SEQ ID NO:24; (c) DNA capable of hybridization to a DNA of (a) under conditions of moderate stringency and which encode pertactin polypeptides; and (d) DNA which is degenerate as a result of the genetic code to a DNA defined in (a), (b) or (c) and which encodes pertactin polypeptides. Pertactin polypeptides encoded by such DNA equivalent sequences are encompassed by the invention.

It will be understood that the present invention is intended to encompass the previously described proteins and polypeptides in isolated or purified form, whether obtained using the techniques described herein or other methods. In a preferred embodiment of this invention, the pertactin polypeptides are substantially free of human or other animal tissue and human or other animal tissue components, nucleic acids, extraneous proteins and lipids, and adventitious microorganisms, such as bacteria and viruses. It will also be understood that the invention encompasses equivalent proteins having substantially the same biological and immunogenic properties. Thus, this invention is intended to cover serotypic variants of the polypeptides of the invention.

Depending on the use to be made of the pertactin polypeptides of the invention, it may be desirable to label them. Examples of suitable labels are radioactive labels, enzymatic labels, fluorescent labels, chemiluminescent labels, and chromophores. The methods for labeling do not differ in essence from those widely used for labeling immunoglobulin. The need to label may be avoided by using labeled antibody to the antigen of the invention or anti-immunoglobulin to the antibodies to the antigen as an indirect marker.

Once the pertactin polypeptides of the invention have been obtained, they can be used to produce polyclonal and monoclonal antibodies reactive therewith. Thus, a protein or polypeptide of the invention can be used to immunize an animal host by techniques known in the art. Such techniques usually involve inoculation, but they may involve other modes of administration. A sufficient amount of the protein or the polypeptide is administered to create an immunogenic response in the animal host. Any host that produces antibodies to the antigen of the invention can be used. Once the animal has been immunized and sufficient time has passed for it to begin producing antibodies to the antigen, polyclonal antibodies can be recovered. The general method comprises removing blood from the animal and separating the serum from the blood. The serum, which contains antibodies to the antigen, can be used as an antiserum to the antigen. Alternatively, the antibodies can be recovered from the serum. Affinity purification is a preferred technique for recovering purified polyclonal antibodies to the antigen, from the serum.

Monoclonal antibodies to the antigens of the invention can also be prepared. One method for producing monoclonal antibodies reactive with the antigens comprises the steps of immunizing a host with the antigen; recovering antibody producing cells from the spleen of the host; fusing the antibody producing cells with myeloma cells deficient in the enzyme hypoxanthine-guanine phosphoribosyl transferase to form hybridomas; select at least one of the hybridomas by growth in a medium comprising hypoxanthine, aminopterin, and thymidine; identifying at least one of the hybridomas that produces an antibody to the antigen, culturing the identified hybridoma to produce antibody in a recoverable quantity; and recovering the antibodies produced by the cultured hybridoma.

These polyclonal or monoclonal antibodies can be used in a variety of applications. Among these is the neutralization of corresponding proteins. They can also be used to detect *Bordetella* antigens in biological preparations or in purifying corresponding proteins, glycoproteins, or mixtures thereof, for example when used in a affinity chromatographic columns.

The pertactin polypeptides of the invention can be used as antigens to identify antibodies to *Bordetella* in materials and to determine the concentration of the antibodies in those materials. Thus, the antigens can be used for qualitative or quantitative determination of *Bordetella* in a material. Such materials, of course, include human or other animal tissue and human or other animal cells, as well as biological fluids, such as human or other animal body fluids, including human sera. When used as a reagent in an immunoassay for determining the presence or concentration of the antibodies to *Bordetella*, the antigens of the present invention provide an assay that is convenient, rapid, sensitive, and specific.

More particularly, the antigens of the invention can be employed for the detection of *Bordetella* by means of immunoassays that are well known for use in detecting or quantifying humoral components in fluids. Thus, antigen-antibody interactions can be directly observed or determined by secondary reactions, such as precipitation or agglutination. In addition, immunoelectrophoresis techniques can also be employed. For example, the classic combination of electrophoresis in agar followed by reaction with anti-serum can be utilized, as well as two-dimensional electrophoresis, rocket electrophoresis, and immunolabeling of polyacrylamide gel patterns (Western Blot or immunoblot.) Other immunoassays in which the antigens of the present invention can be employed include, but are not limited to, radioimmunoassay, competitive immunoprecipitation assay, enzyme immunoassay, and immunofluorescence assay. It will be understood that turbidimetric, calorimetric, and nephelometric techniques can be employed. An immunoassay based on Western Blot technique is preferred.

Immunoassays can be carried out by immobilizing one of the immunoreagents, either an antigen of the invention or an antibody of the invention to the antigen, on a carrier surface while retaining immunoreactivity of the reagent. The reciprocal immunoreagent can be unlabeled or labeled in such a manner that immunoreactivity is also retained. These techniques are especially suitable for use in enzyme immunoassays, such as enzyme linked immunosorbent assay (ELISA) and competitive inhibition enzyme immunoassay (CIEIA).

When either the antigen of the invention or antibody to the antigen is attached to a solid support, the support is usually a glass or plastic material. Plastic materials molded in the form of plates, tubes, beads, or disks are preferred. Examples of suitable plastic materials are polystyrene and polyvinyl chloride. If the immunoreagent does not readily bind to the solid support, a carrier material can be interposed between the reagent and the support. Examples of suitable carrier materials are proteins, such as bovine serum albumin, or chemical reagents, such as gluteraldehyde or urea. Coating of the solid phase can be carried out using conventional techniques.

The invention provides immunogenic pertactin polypeptides, and more particularly, protective polypeptides for use in the preparation of vaccine compositions against *Bordetella*. These polypeptides can thus be employed as vaccines by administering the polypeptides to a mammal susceptible to *Bordetella* infection. Conventional modes of administration can be employed. For example, administration can be carried out by oral, respiratory, or parenteral routes. Intradermal, subcutaneous, and intramuscular routes of administration are preferred when the vaccine is administered parenterally.

The major purpose of the immune response in a *Bordetella*-infected mammal is to inactivate the *Bordetella* and to eliminate *Bordetella* infected cells that have the potential to release infectious virus. The B-cell arm of the immune response has the major responsibility for inactivating *Bordetella*. The principal manner in which this is achieved is by neutralization of infectivity. Another major mechanism for destruction of the *Bordetella*-infected cells is provided by cytotoxic. T lymphocytes (CTL) that recognize pertactin antigens expressed in combination with class I histocompatibility antigens at the cell surface. The CTLs recognize pertactin polypeptides processed within cells from a pertactin protein that is produced, for example, by the infected cell or that is internalized by a phagocytic cell. Thus, this invention can be employed to stimulate a B-cell response to pertactin polypeptides, as well as immunity mediated by a CTL response following infection. The CTL response can play an important role in mediating recovery from primary *Bordetella* infection and in accelerating recovery during subsequent infections.

The ability of the pertactin polypeptides and vaccines of the invention to induce protective levels of neutralizing antibody in a host can be enhanced by emulsification with an adjuvant, incorporating in a liposome, coupling to a suitable carrier, or by combinations of these techniques. For example, the pertactin polypeptides of the invention can be administered with a conventional adjuvant, such as aluminum phosphate and aluminum hydroxide gel, in an amount sufficient to potentiate humoral or cell-mediated immune response in the host. Similarly, the pertactin polypeptides can be bound to lipid membranes or incorporated in lipid membranes to form liposomes. The use of nonpyrogenic lipids free of nucleic acids and other extraneous matter can be employed for this purpose.

The immunization schedule will depend upon several factors, such as the susceptibility of the host to infection and the age of the host. A single dose of the vaccine of the invention can be administered to the host or a primary course of immunization can be followed in which several doses at intervals of time are administered. Subsequent doses used as boosters can be administered as need following the primary course.

The pertactin proteins, polypeptides, and vaccines of the invention can be administered to the host in an amount sufficient to prevent or inhibit *Bordetella* infection or replication in vivo. In any event, the amount administered should be at least sufficient to protect the host against substantial immunosuppression, even though *Bordetella* infection may not be entirely prevented. An immunogenic response can be obtained by administering the proteins or polypeptides of the invention to the host in an amount of, for example, about 1 to about 50 micrograms antigen per kilogram of body weight, preferably about 5 to about 10 micrograms antigen per kilogram of body weight. The proteins, polypeptides, and vaccines of the invention can be administered together with a physiologically acceptable carrier. For example, a diluent, such as water or a saline solution, can be employed.

Another aspect of the invention includes administering any combination of the nucleic acids encoding pertactin polypeptides, the proteins, and polypeptides per se, with or without carrier molecules, to an individual. The individual can be an animal. As used herein, the term “animal” means a mammal, and preferably, the mammal is selected from the group consisting of a human, a rabbit, a mouse, a dog, a cat, a bovine, a pig, and a horse. In an especially preferred embodiment, the mammal is a human.

The methods of treating include administering immunogenic compositions comprising pertactin proteins or polypeptides, and compositions comprising nucleic acids encoding pertactin proteins or polypeptides as well. Those of skill in the art are cognizant of the concept, application, and effectiveness of nucleic acid vaccines (e.g., DNA vaccines) and nucleic acid vaccine technology as well as protein and polypeptide based technologies. The nucleic acid based technology allows the administration of nucleic acids encoding pertactin polypeptides, naked or encapsulated, directly to tissues and cells without the need for production of encoded proteins prior to administration. The technology is based on the ability of these nucleic acids to be taken up by cells of the recipient organism and expressed to produce an immunogenic determinant to which the recipient’s immune system responds. Typically, the expressed antigens are displayed on the surface of cells that have taken up and expressed the nucleic acids, but expression and export of the encoded antigens into the circulatory system of the recipient individual is also within the scope of the present invention. Such nucleic acid vaccine technology includes, but is not limited to, delivery of naked DNA and RNA and delivery of expression vectors encoding pertactin polypeptides. Although the technology is termed “vaccine”, it is equally applicable to immunogenic compositions that do not result in a protective response. Such non-protection inducing compositions and methods are encompassed within the present invention.

Although it is within the present invention to deliver nucleic acids encoding pertactin polypeptides and carrier molecules as naked nucleic acid, the present invention also encompasses delivery of nucleic acids as part of larger or more complex compositions. Included among these delivery systems are viruses, virus-like particles, or bacteria containing the nucleic acid encoding pertactin polypeptides. Also, complexes of the invention’s nucleic acids and carrier molecules with cell permeabilizing compounds, such as liposomes, are included within the scope of the invention. Other compounds, such as molecular vectors (EP 696,191, Samain et al.) and delivery systems for nucleic acid vaccines are known to the skilled artisan and exemplified in, for example, WO 93 06223 and WO 90 11092, U.S. Pat. No. 5,580,859, and U.S. Pat. No. 5,589,466 (Vical patents), which are incorporated by reference herein, and can be made and used without undue or excessive experimentation.

To further achieve the objects and in accordance with the purposes of the present invention, a kit capable of diagnosing a *Bordetella* infection is described. This kit, in one embodiment, contains the DNA sequences of this invention, which are capable of hybridizing to bacterial RNA or analogous DNA sequences to indicate the presence of a *Bordetella* infection. Different diagnostic techniques can be used which include, but are not limited to: (1) Southern blot procedures to identify cellular DNA which may or may not be digested with restriction enzymes; (2) Northern blot techniques to identify RNA extracted from cells; and (3) dot blot techniques, i.e., direct filtration of the sample through a membrane, such as nitrocellulose or nylon, without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by centrifugation.

Following are references of the strains used in the search concerning the present invention:

9.73H+5, DEL, SEI: Infect Immun. (1993) 61 "4072-4078. Gueirard, P. and Guiso, N., filed with CNCM on May 12, 1989, No. 858.

CVGEO identical to strain CVHAI 286, 335: Microbiol. (1997) 143:1433-1441. Le Blay, K. et al.

63.2: CIP—Lab. Ident., Inst. Pasteur, Paris, France—J. Clin. Microbiol., 1993, 31, 2745

TI: CIP81.32—Lab. Ident., Inst. Pasteur, Paris, France—J. Clin. Microbiol., 1993, 31, 2746

Fr287: Vaccine (1999) 17:2651:2660. Boursaux-Eude, C. et al.

18232: ref OMS: ATCC97.97 (CIP63.1).

REFERENCES

The following references have been cited in this application. The entire disclosure of each of these references is relied upon and incorporated by reference herein.

1. Arico, B., R. Gross, J. Smida, and R. Rappuoli. 1987. Evolutionary relationships in the genus *Bordetella*. Mol. Microbiol. 1:301-308.
2. Arico, B., J. F. Miller, C. Roy, S. Stibitz, D. Monack, S. Falkow, R. Gross, and R. Rappuoli. 1989. Sequences required for expression of *Bordetella pertussis* virulence factors share homology with prokaryotic signal transduction proteins. Proc. Natl. Acad. Sci. USA. 86:6671-6675.
3. Boursaux-Eude, C., G. Thiberge, G. Carletti, and N. Guiso. 1999. Intranasal murine model of *Bordetella pertussis* infection: II. Sequence variation and protection induced by a tricomponent acellular vaccine. Vaccine. Infect. Immum. 56:3189-3195.

4. Brennan, M. J., Z. M. Li, J. L. Cowell, M. E. Bisher, A. C. Steven, P. Novotny, and C. R. Manclark. 1988. Identification of a 69-kilodalton nonfimbrial protein as an agglutinogen of *Bordetella pertussis*. Infect. Immun. 56:3189-3195.

5. Charles, I. G., G. Dougan, D. Pickard, S. Chatfield, M. Smith, P. Novotny, P. Morrissey, and N. F. Fairweather. 1989. Molecular cloning and characterization of protective outer membrane protein P.69 from *Bordetella pertussis*. Proc. Natl. Acad. Sci. USA. 86:3554-3558.

6. Charles, I. G., J. L. Li, M. Roberts, K. Beesley, M. Romanos, D. J. Pickard, M. Francis, D. Campbell, G. Dougan, M. J. Brennan, C. R. Manclarek, M. A. Jensen, I. Heron, A. Chubb, P. Novotny, and N. F. Fairweather. 1991. Identification and characterization of a protective immunodominant B cell epitope of pertactin (P.69) from *Bordetella pertussis*. Eur. J. Immunol. 21:1147-1153.

7. Goodnow, R.A. 1980. Biology of *Bordetella bronchiseptica*. Microbiol. Rev. 44:722-738.

8. Gueirard, P., C. Weber, A. Le Coustumier, and N. Guiso. 1995. Human *Bordetella bronchiseptica* infection related to contact with infected animals: persistence of bacteria in host. J. Clin. Microbiol. 33:2002-2006.

9. Hewlett, E. L., and J. D. Cherry. 1997. New and improved vaccines against pertussis, vol. 2nd. Coordinating eds., M. M. Levine, G. C. Woodrow, J. B. Kaper, and G. S. Cobon. Marcel Dekker, New York.

10. Higgins, D. G., and P. M. Sharp. 1988. CLUSTAL: a package for performing multiple sequence alignment on a microcomputer. Gene. 73:237-244.

11. Khelef, N., B. Danve, M. J. Quentin-Millet, and N. Guiso. 1993. *Bordetella pertussis* and *Bordetella parapertussis*: two immunologically distinct species. Infect. Immun. 61:486-490.

12. Kobisch, M., and P. Novotny. 1990. Identification of a 68-kilodalton outer membrane protein as the major protective antigen of *Bordetella bronchiseptica* by using specific-pathogen-free piglets. Infect. Immun. 58:352-357.

13. Leininger, E., M. Roberts, J. G. Kenimer, I. G. Charles, N. Fairweather, P. Novotny, and M. J. Brennan. 1991. Pertactin, an Arg-Gly-Asp-containing *Bordetella pertussis* surface protein that promotes adherence of mammalian cells. Proc. Natl. Acad. Sci. USA. 88:345-349.

14. Li, J., N. F. Fairweather, P. Novotny, G. Dougan, and I. G. Charles. 1992. Cloning, nucleotide sequence and heterologous expression of the protective outer-membrane protein P.68 pertactin from *Bordetella bronchiseptica*. J. Gen. Microbiol. 138:1697-1705.

15. Li, L. J., G. Dougan, P. Novotny, and I. G. Charles. 1991. P.70 pertactin, an outer-membrane protein from *Bordetella parapertussis*: cloning, nucleotide sequence and surface expression in *Escherichia coli*. Mol. Microbiol. 5:409-417.

16. Montaraz, J. A., P. Novotny, and J. Ivanyi. 1985. Identification of a 68-kilodalton protective protein antigen from *Bordetella bronchiseptica*. Infect. Immun. 47:744-751.

17. Mooi, F. R., H. van Oirschot, K. Heuvelman, H. G. J. van der Heide, W. Gaastra, and R. J. L. Willems. 1998. Polymorphism in the *Bordetella pertussis* virulence factors P.69/pertactin and pertussis roxin in the Netherlands: Temporal trends and evidence doe vaccine-driven evolution. Infect. Immun. 66:670-675.

18. Novotny, P., A. P. Chubb, K. Cownley, J. A. Montaraz, and J. E. Beesley. 1985. *Bordetella* adenylate cyclase: a genus specific protective antigen and virulence factor. Develp. Biol. Standard. 61:27-41.

19. Novotny, P., M. Kobisch, K. Cownley, A. P. Chubb, and J. A. Montaraz. 1985. Evaluation of *Bordetella bronchiseptica* vaccines in specific-pathogen-free piglets with bacterial cell surface antigens in enzyme-linked immunosorbent assay. Infect. Immun. 50:190-198.

20. Shahin, R. D., M. J. Brennan, Z. M. Li, B. D. Meade, and C. R. Manclark. 1990. Characterization of the protective capacity and immunogenicity of the 69-kD outer membrane protein of *Bordetella pertussis*. J. Exp. Med. 171:63-73.

21. Stibitz, S., W. Aaronson, D. Monack, and S. Falkow. 1989. Phase variation in *Bordetella pertussis* by frameshift mutation in a gene for a novel two-component system. Nature. 338:266-269.

22. Woolfrey, B. F., and J. A. Moody. 1991. Human infections associated with *Bordetella bronchiseptica*. Clin. Microbiol. Rev. 4:243-255.

*B. bronchiseptica* p.68 pertactin gene

[SEQ ID NO:1]

```
atcgatgatg cgtcgctgta acacggcaaa taccgtgcat tgcagcggtt ctggatggcg

ttcttcgtac gtttgctgcg cccattcttc cctgttccat cgcggtgcgg ccatggcggg

cgtctgctct tcacccggca tccaatgaac atgtctctgt cacgcattgt cttggcggcg

cccctgcgcc gcaccacact ggccatggcg ctgggcgcgc tgggcgccgc gcccgccgcg

tacgccgact ggaacaacca gtccatcatc aaggccggcg agcgccagca cggcatccac

atcaagcaaa gcgatggcgc cggcgtacgg accgccaccg gaacgaccat caaggtaagc

ggtcgtcagg cccagggcgt cctgctggaa aatcccgcgg ccgagctgcg gttccagaac

ggcagcgtca cgtcttcggg acagctgttc gacgaaggcg tccggcgctt tctgggcacc

gtcaccgtca aggccggcaa gctggtcgcc gatcacgcca cgctggccaa cgtcagcgac

acccgggacg acgacggcat cgcgctctat gtggccggcg agcaggccca ggccagcatc

gccgacagca ccctgcaggg cgcgggcggc gtgcgggtcg agcgcggcgc caatgtcacg
```

-continued

```
gtccaacgca gcaccatcgt tgacgggggc ttgcatatcg gcaccctgca gccgctgcag

ccggaagacc ttccgcccag ccgggtggtg ctgggcgaca ccagcgtgac cgccgtgccc

gccagcggcg cgcccgcggc ggtgtctgta ttcggggcca atgagcttac ggttgatggc

gggcacatca ccgggggcg ggcagcgggg gtggcggcca tggacggggc gatcgtgcat

ctg[cagcgcg cgacgatacg gcggggggac gcgcctgccg gcggtgcggt tccaggcggt

gctgttcccg gcggcttcgg ccccctcctt gacggctggt atggcgtgga tgtatcggat

tccaccgtgg acctcgctca g]*tcgatcgtc gaggcgccgc agctgggcgc cgcgatccgg

gcgggccgcg gcgccagggt gacggtgtcg ggcggcagct tgtccgcacc gcacggcaat

gtcatcgaga ccggcggcgg cgcgcgtcgc ttcccgcctc cggcctcgcc cctgtcgatc

accttgcagg cgggcgcacg ggcgcagggg agggcgctgc tgtaccgggt cctgccggag

cccgtgaagc tgacgctggc gggcggcgcc caggggcagg gcgacatcgt cgcgacggag

ctgcctccca ttccaggcgc gtcgagcggg ccgctcgacg tggcgctggc cagccaggcc
* Region I

cgatggacgg gcgctacccg cgcggtcgac tcgctgtcca tcgacaacgc cacctgggtc

atgacggaca actcgaacgt cggcgcgctg cggctggcca gcgacggcag cgtcgatttc

cagcagccgg ccgaagctgg gcggttcaag tgcctgatgg tcgatacgct ggcgggttcg

gggctgttcc gcatgaatgt cttcgcggac ctggggctga gcgacaagct ggtcgtcatg

cgggacgcca gcggccagca caggctgttg gtccgcaaca gcggcagcga gccggccagc

ggcaacacca tgctgctggt gcagacgcca cgaggcagcg cggcgacctt tacccttgcc

aacaaggacg gcaaggtcga tatcggtacc taccgctatc gattggccgc caacggcaat

gggcagtgga gcctggtg[gg cgcgaaggcg ccgccggcgc ccaagcccgc gccgcagccc

ggtccccagc ccggtcccca gccgccgcag ccgccgcagc cgccgcagcc gccacagagg

cagccggaag cgccggcgcc gcaaccgccg gcgggcaggg agttgtccgc cgcc]**gccaac

gcggcggtca acacgggtgg ggtgggcctg gccagcacgc tctggtacgc cgaaagcaat

gcgttgtcca agcgcctggg cgagttgcgc ctgaatccgg acgccggcgg cgcttggggc

cgcggcttcg cgcaacgcca gcaactggac aaccgcgccg ggcggcgctt cgaccagaag

gtggccggct tcgagctggg cgccgaccac gcggtggcgg tggccggcgg gcgctggcac

ctgggcgggc tggccggcta tacgcgcggc gaccgcggct ttaccggcga cggcggcggc

cacaccgaca gcgtgcatgt cgggggctat gccacctata tcgccaacag cggtttctac

ctggacgcga cgctgcgcgc cagccgcctc gaaaatgact tcaaggtggc gggcagcgat

gggtacgcgg tcaagggcaa gtaccgcacc catggggtag gcgcctcgct cgaggcgggc

cggcgcttcg cccatgccga cggctggttc ctcgagccgc aggccgagct ggcggtgttc

cgggtcggcg gcggttcgta ccgcgcggcc aatggcctgc gggtgcgcga cgaaggcggc

agctcggtgc tgggtcgcct gggcctggag gtcggcaagc gcatcgaact ggcaggcggc

aggcaggtgc agccatacat caaggccagc gtgctgcagg agttcgacgg cgcgggtacg

gtacgcacca acggcatcgc gcaccgcacc gaactgcgcg gcacgcgcgc cgaactgggc

ctgggcatgg ccgccgcgct gggccgcggc cacagcctgt atgcctcgta cgagtactcc

aagggcccga agctggccat gccgtggacc ttccacgcgg gctaccggta cagctggtaa
** Region II

agcgagaagg gtccatccCC ccgcggggga gattttcctg gaggttggcc ggtgccagtc

tccaggctca ggcggccagg gcgtgcgggc cgggcaggcc gtgctggtgc tggccgaacc
```

-continued

*B. bronchiseptica* p.68 pertactin protein

[SEQ ID NO:4]

MNMSLSRIVL AAPLRRTTLA MALGALGAAP AAYADWNNQS IIKAGERQHG IHIKQSDGAG

VRTATGTTIK VSGRQAQGVL LENPAAELRF QNGSVTSSGQ LFDEGVRRFL GTVTVKAGKL

VADHATLANV SDTRDDDGIA LYVAGEQAQA SIADSTLQGA GGVRVERGAN VTVQRSTIVD

GGLHIGTLQP LQPEDLPPSR VVLGDTSVTA VPASGAPAAV SVFGANELTV DGGHITGGRA

AGVAAMDGAI VHL[QRATIRR GDAPAGGAVP GGAVPGGFGP LLDGWYGVDV SDSTVDLAQ]*S

IVEAPQLGAA IRAGRGARVT VSGGSLSAPH GNVIETGGGA RRFPPPASPL SITLQAGARA

QGRALLYRVL PEPVKLTLAG GAQGQGDIVA TELPPIPGAS SGPLDVALAS QARWTGATRA

VDSLSIDNAT WVMTDNSNVG ALRLASDGSV DFQQPAEAGR FKCLMVDTLA GSGLFRMNVF

ADLGLSDKLV VMRDASGQHR LLVRNSGSEP ASGNTMLLVQ TPRGSAATFT LANKDGKVDI

GTYRYRLAAN GNGQWSLV[GA KAPPAPKPAP QPGPQPGPQP PQPPQPPQPP QRQPEAPAPQ

PPAGRELSAA]** ANAAVNTGGV GLASTLWYAE SNALSKRLGE LRLNPDAGGA WGRGFAQRQQ

LDNRAGRRFD QKVAGFELGA DHAVAVAGGR WHLGGLAGYT RGDRGFTGDG GGHTDSVHVG

GYATYIANSG FYLDATLRAS RLENDFKVAG SDGYAVKGKY RTHGVGASLE AGRRFAHADG

WFLEPQAELA VFRVGGGSYR AANGLRVRDE GGSSVLGRLG LEVGKRIELA GGRQVQPYIK

ASVLQEFDGA GTVRTNGIAH RTELRGTRAE LGLGMAAALG RGHSLYASYE YSKGPKLANP

WTFHAGYRYS W

* Region I

** Region II

*B. pertussis* p.69 gene

[SEQ ID NO:2]

atgaacatgt ctctgtcacg cattgtcaag gcggcgcccc tgcgccgcac cacgctggcc atggcgctgg gcgcgctggg cgccgccccg gcggcgcatg ccgactggaa caaccagtcc atcgtcaaga ccggtgagcg ccagcatggc atccatatcc agggctccga cccgggcggc gtacggaccg ccagcggaac caccatcaag gtaagcggcc gtcaggccca gggcatcctg ctagaaaatc ccgcggccga gctgcagttc cggaacggca gtgtcacgtc gtcgggacag ttgtccgacg atggcatccg gcgctttctg ggcaccgtca ccgtcaaggc cggcaagctg gtcgccgatc acgccacgct ggccaacgtt ggcgacacct gggacgacga cggcatcgcg ctctatgtgg ccggcgaaca ggcccaggcc agcatcgccg acagcaccct gcagggcgct ggcggcgtgc agatcgagcg cggcgccaat gtcacggtcc aacgcagcgc catcgtcgac gggggcttgc atatcggcgc cctgcagtca ttgcagccgg aagaccttcc gcccagccgg gtggtgctgc gcgacaccaa cgtgaccgcc gtgcccgcca gcggcgcgcc cgcggcggtg tctgtgttgg gggccagtga gcttacgctc gacggcgggc acatcaccgg cgggcgggca gcgggggtgg cggccatgca aggggcggtc gtgcatctg[c agcgcgcgac gatacggcgc ggggacgcgc ctgccggcgg tgcggttccc ggcggtgcgg ttcccggtgg tgcggttccc ggcggcttcg gtcccggcgg cttcggtccc gtcctcgacg gctggtatgg cgtggacgta tcgggctcca gcgtggagct cgcccag]*tcg atcgtcgagg cgccggagct gggcgccgca atccgggtgg gccgcggcgc cagggtgacg gtgtcgggcg gcagcttgtc cgcaccgcac ggcaatgtca tcgagaccgg cggcgcgcgt cgctttgcgc ctcaagccgc gcccctgtcg atcaccttgc aggccggcgc gcatgcccag gggaaagcgc tgctgtaccg ggtcctgccg gagcccgtga agctgacgct gaccgggggc gccgatgcgc agggcgacat cgtcgcgacg gagctgccct ccattcccgg cacgtcgatc gggccgctcg acgtggcgct ggccagccag -continued gcccgatgga cgggcgctac ccgcgcggtc gactcgctgt ccatcgacaa cgccacctgg gtcatgacgg acaactcgaa cgtcggtgcg ctacggctgg ccagcgacgg cagcgtcgat
* Region I ttccagcagc cggccgaagc tgggcggttc aaggtcctga cggtcaatac gctggcgggt tcggggctgt tccgcatgaa tgtcttcgcg gacctggggc tgagcgacaa gctggtcgtc atgcaggacg ccagcggcca gcacaggctg tgggtccgca acagcggcag cgagccggcc agcgccaaca ccctgctgct ggtgcagacg ccacgaggca gcgcggcgac ctttaccctt gccaacaagg acggcaaggt cgatatcggt acctatcgct atcgattggc cgccaacggc aatgggcagt ggagcctggt g[ggcgcgaag gcgccgccgg cgcccaagcc cgcgccgcag ccgggtcccc agccgccgca gccgccgcag ccgcagccgg aagcgccggc gccgcaaccg ccggcgggca gggagttgtc cgccgcc]**gcc aacgcggcgg tcaacacggg tggggtgggc ctggccagca cgctctggta cgccgaaagc aatgcgttgt ccaagcgcct gggcgagttg cgcctgaatc cggacgccgg cggcgcctgg ggccgcggct tcgcgcaacg ccagcagctg gacaaccgcg ccgggcggcg cttcgaccag aaggtggccg gcttcgagct gggcgccgac cacgcggtgg cggtggccgg cggacgctgg cacctgggcg ggctggccgg ctatacgcgc ggcgaccgcg gcttcaccgg cgacggcggc ggccacaccg acagcgtgca tgtcgggggc tatgccacat atatcgccga cagcggtttc tacctggacg cgacgctgcg cgccagccgc ctggagaatg acttcaaggt ggcgggcagc gacgggtacg cggtcaaggg caagtaccgc acccatgggg tgggcgcctc gctcgaggcg ggccggcgct ttacccatgc cgacggctgg ttcctcgagc cgcaggccga gctggcggta ttccgggccg gcggcggtgc gtaccgcgcg gccaacggcc tgcgggtgcg cgacgaaggc ggcagctcgg tgctgggtcg cctgggcctg gaggtcggca agcgcatcga actggcaggc ggcaggcagg tgcagccata catcaaggcc agcgtgctgc aggagttcga cggcgcgggt acggtacaca ccaacggcat cgcgcaccgc accgaactgc gcggcacgcg cgccgaactg ggcctgggca tggccgccgc gctgggccgc ggccacagcc tgtatgcctc gtacgagtac tccaagggcc cgaagctggc catgccgtgg accttccacg cgggctaccg gtacagctgg taa
** Region II

*B. pertussis* p.69 protein
[SEQ ID NO:5]

MNMSLSRIVK AAPLRRTTLA MALGALGAAP AAHADWNNQS IVKTGERQHG IHIQGSDPGG

VRTASGTTIK VSGRQAQGIL LENPAAELQF RNGSVTSSGQ LSDDGIRRFL GTVTVKAGKL

VADHATLANV GDTWDDDGIA LYVAGEQAQA SIADSTLQGA GGVQIERGAN VTVQRSAIVD

GGLHIGALQS LQPEDLPPSR VVLRDTNVTA VPASGAPAAV SVLGASELTL DGGHITGGRA

AGVAAIYIQGAV VHL[QRATIRR GDAPAGGAVP GGAVPGGAVP GGFGPGGFGP VLDGWYGVDV

SGSSVELAQ]*S IVEAPELGAA IRVGRGARVT VSGGSLSAPH GNVIETGGAR RFAPQAAPLS

ITLQAGAHAQ GKALLYRVLP EPVKLTLTGG ADAQGDIVAT ELPSIPGTSI GPLDVALASQ

ARWTGATRAV DSLSIDNATW VMTDNSNVGA LRLASDGSVD FQQPAEAGRF KVLTVNTLAG

SGLFRMNVFA DLGLSDKLVV MQDASGQHRL WVRNSGSEPA SANTLLLVQT PRGSAATFTL

ANKDGKVDIG TYRYRLAANG NGQWSLV[GAK APPAPKPAPQ PGPQPPQPPQ PQPEAPAPQP

PAGRELSAA]**A NAAVNTGGVG LASTLWYAES NALSKRLGEL RLNPDAGGAW GRGFAQRQQL

DNRAGRRFDQ KVAGFELGAD HAVAVAGGRW HLGGLAGYTR GDRGFTGDGG GHTDSVHVGG

YATYIADSGF YLDATLRASR LENDFKVAGS DGYAVKGKYR THGVGASLEA GRRFTHADGW

-continued

FLEPQAELAV FRAGGGAYRA ANGLRVRDEG GSSVLGRLGL EVGKRIELAG GRQVQPYIKA

SVLQEFDGAG TVHTNGIAHR TELRGTRAEL GLGMAAALGR GHSLYASYEY SKGPKLAMPW

T FHAGYRYSW
*  Region I
** Region II

*B. parapertussis* p.70 gene

[SEQ ID NO:3]

atcgatgatg cgtcgctgta acacggcaaa taccgtgcat tgcagcggtt ctggatggcg ttcttcgtac gtttgctgcg cccattcttc cctgttccat cgcggtgcgg gcatggcggg cgtctgCtCt tcacccggca tccaatgaac atgtctctgt cacgcattgt caaggcggcg cccctgcgcC gcaccacact ggccatggcg ctgggcgcgc tgggcgccgc gcccgccgcg tacgccgact ggaacaacca gtccatcatc aaggccggcg agcgccagca cggcatccac atcaagcaaa gcgatggcgc cggcgtacgg accgccaccg gaacgaccat caaggtaagc ggtcgtcagg cccagggcgt cctgctggaa aatcccgcgg ccgagctgcg gttccagaac ggcagcgtca cgtcttcggg acagctgttc gacgaaggcg tccggcgctt tctgggcacc gtcaccgtca aggccggcaa gctggtcgcc gatcacgcca cgctggccaa cgtcagcgac acccgggacg acgacggcat cgcgctctat gtggccggcg agcaggccca ggccagcatc gccgacagca ccctgcaggg cgcgggcggc gtgcgggtcg agcgcggcgc caatgtcacg gtccaacgca gcaccatcgt tgacgggggc ttgcatatcg gcaccctgca gccgctgcag ccggaagacc ttccgcccag ccgggtggtg ctgggcgaca ccagcgtgac cgccgtgccc gccagcggcg cgcccgcggc ggtgtttgta ttcggggcca atgagcttac ggttgatggc gggcacatca ccgggggcgg ggcagcgggg gtggcggcca tggacggggc gatcgtgcat ctg[cagcgcg cgacgatacg gcggggggac gcgcctgccg gcggtgcggt tccaggcggt gcggttcccg gcggtgccgt tcccggcggc ttcggccccc tccttgacgg ctggtatggc gtggatgtat cggactccac cgtggacctc gctcag]*tcga tcgtcgaggc gccgcagctg ggcgccgcga tccgggcggg ccgcggcgcc agggtgacgg tgtcgggcgg cagcttgtcc gcaccgcacg gcaatgtcat cgagaccggc ggcggtgcgc gtcgcttccc gcctccggcc tcgcccctgt cgatcacctt gcaggcgggc gcacgggcgc aggggagggc gctgctgtac cgggtcctgc cggagcccgt gaagctgacg ctggcgggcg gcgcccaggg gcagggcgac atcgtcgcga cggagctgcc tcccattcca ggcgcgtcga gcgggccgct cgacgtggcg ctggccagcc aggcccgatg gacgggcgct acccgcgcgg tcgactcgct gtccatcgac aacgccacct gggtcatgac ggacaactcg aacgtcggcg cgctgcggct ggccagcgac ggcagcgtcg atttccagca gccggccgaa gctgggcggt tcaaggtcct gatggtcgat acgctggcgg gttcggggct gttccgcatg aatgtcttcg cggacctggg gctgagcgac aagctggtcg tcatgcggga cgccagcggc cagcacaggc tgtgggtccg caacagcggc agcgagccgg ccagcggcaa caccatgctg ctggtgcaga cgccacgagg cagcgcggcg
* Region I acctttaccc ttgccaacaa ggacggcaag gtcgatatcg gtacctaccg ctatcgattg gccgccaacg gcaatgggca gtggagcctg gtg[ggcgcga aggcgccgcc ggcgcccaag cccgcgccgc agcccggtcc ccagcccggt ccccagccgc cgcagccgcc gcagccgccg cagccgccgc agccgccgca gccgccacag aggcagccgg aagcgccggc gccgcaaccg ccggcgggca gggagttgtc cgccgcc]**gcc aacgcggcgg tcaacacggg tggggtgggc ctggccagca cgctctggta cgccgaaagc aatgcgttgt ccaagcgcct gggcgagttg -continued cgcctgaatc cggacgccgg cggcgcttgg ggccgcggct tcgcgcaacg ccagcaactg gacaaccgcg ccgggcggcg cttcgaccag aaggtggccg gcttcgagct gggcgccgac cacgcggtgg cggtggccgg cgggcgctgg cacctgggcg ggctggccgg ctatacgcgc ggcgaccgcg gctttaccgg cgacggcggc ggccacaccg acagcgtgca tgtcgggggc tatgccacct atatcgccaa cagcggtttc tacctggacg cgacgctgcg cgccagccgc ctcgaaaatg acttcaaggt ggcgggcagc gatgggtacg cggtcaaggg caagtaccgc acccatgggg taggcgtctc gctcgaggcg ggccggcgct tcgcccatgc cgacggctgg ttcctcgagc cgcaggccga gctggcggtg ttccgggtcg gcggcggtgc gtaccgcgcg gccaatggcc tgcgggtgcg cgacgaaggc ggcagctcgg tgctgggtcg cctgggcctg gaggtcggca agcgcatcga actggcaggc ggcaggcagg tgcagccata catcaaggcc agcgtgttgc aggagttcga cggcgcgggt acggtacgca ccaacggcat cgcgcatcgc accgaactgc gcggcacgcg cgccgaactg ggcctgggca tggccgccgc gctgggccgc ggccacagcc tgtatgcctc gtacgagtac tccaagggcc cgaagctggc catgccgtgg accttccacg cgggctaccg gtacagctgg taaagcgaga agggtccatc ccccgcggag gagtttttcc tggaggttgg ccggtgccag tctccaggct caggcggcca gggcctgcgg gccgggcagg ccgtgctggt gctggccgaa ccattgcaca gggtgttcgg ccaagggcgg cgacttcgcc gatgaccagc aacgccgggg ggcgcacgct gcgccggcgc gcgatc

** Region I

*B. parapertussis* p.70 protein

[SEQ ID NO:6]

MNMSLSRIVK AAPLRRTTLA MALGALGAAP AAYADWNNQS IIKAGERQHG IHIKQSDGAG

VRTATGTTIK VSGRQAQGVL LENPAAELRF QNGSVTSSGQ LFDEGVRRFL GTVTVKAGKL

VADHATLANV SDTRDDDGIA LYVAGEQAQA SIADSTLQGA GGVRVERGAN VTVQRSTIVD

GGLHIGTLQP LQPEDLPPSR VVLGDTSVTA VPASGAPAAV FVFGANELTV DGGHITGGRA

AGVAAMDGAI VHL[QRATIRR GDAPAGGAVP GGAVPGGAVP GGFGPLLDGW YGVDVSDSTV

DLAQ]*SIVEAP QLGAAIRAGR GARVTVSGGS LSAPHGNVIE TGGGARRFPP PASPLSITLQ

AGARAQGRAL LYRVLPEPVK LTLAGGAQGQ GDIVATELPP IPGASSGPLD VALASQARWT

GATPAVDSLS IDNATWVMTD NSNVGALRLA SDGSVDFQQP AEAGRFKVLM VDTLAGSGLF

RMNVFADLGL SDKLVVMRDA SGQHRLWVRN SGSEPASGNT MLLVQTPRGS AATFTLANKD

GKVDIGTYRY RLAANGNGQW SLV[GAKAPPA PKPAPQPGPQ PGPQPPQPPQ PPQPPQPPQP

PQRQPEAPAP QPPAGRELSA A]**ANAAVNTGG VGLASTLWYA ESNALSKRLG ELRLNPDAGG

AWGRGFAQRQ QLDNPAGRRF DQKVAGFELG ADHAVAVAGG RWRLGGLAGY TRGDRGFTGD

GGGHTDSVHV GGYATYIANS GFYLDATLRA SRLENDFKVA GSDGYAVKGK YRTHGVGVSL

EAGRRFAHAD GWFLEPQAEL AVFRVGGGAY RAANGLRVRD EGGSSVLGRL GLEVGKRIEL

AGGRQVQPYI KASVLQEFDG AGTVRTNGIA HRTELRGTRA ELGLGMAAAL GRGHSLYASY

EYSKGPKLAN PWTFHAGYRY SW

* Region I

** Region II

What is claimed is:

1. An isolated polypeptide consisting of the amino acids is SEQ ID NO: 7.

2. A diagnostic kit for the detection of the presence or absence of antibodies, which bind a polypeptide consisting of the amino acids in SEQ ID NO: 7, wherein the kit comprises an antigen comprising a polypeptide consisting of the amino acids in SEQ ID NO: 7, and means for detecting the formation of immune complex between the antigen and antibodies, wherein the means are present in an amount sufficient to perform said detection.

3. An immunogenic composition comprising a polypeptide consisting of the amino acids in SEQ ID NO: 7 in an amount sufficient to induce an immunogenic or protective response in vivo, and a pharmaceutically acceptable carrier therefor.

* * * * *

SEQUENCE LISTING

<160> NUMBER OF SEQ ID NOS: 25

<210> SEQ ID NO 1
<211> LENGTH: 3000
<212> TYPE: DNA
<213> ORGANISM: Bordetella bronchiseptica

<400> SEQUENCE: 1
atcgatgatg cgtcgctgta acacggcaaa taccgtgcat tgcagcggtt ctggatggcg 60
ttcttcgtac gtttgctgcg cccattcttc cctgttccat cgcggtgcgg ccatggcggg 120
cgtctgctct tcacccggca tccaatgaac atgtctctgt cacgcattgt cttggcggcg 180
cccctgcgcc gcaccacact ggccatggcg ctgggcgcgc tgggcgccgc gcccgccgcg 240
tacgccgact ggaacaacca gtccatcatc aaggccggcg agcgccagca cggcatccac 300
atcaagcaaa gcgatggcgc cggcgtacgg accgccaccg gaacgaccat caaggtaagc 360
ggtcgtcagg cccagggcgt cctgctggaa aatcccgcgg ccgagctgcg gttccagaac 420
ggcagcgtca cgtcttcggg acagctgttc gacgaaggcg tccggcgctt tctgggcacc 480
gtcaccgtca aggccggcaa gctggtcgcc gatcacgcca cgctggccaa cgtcagcgac 540
acccgggacg acgacggcat cgcgctctat gtggccggcg agcaggccca ggccagcatc 600
gccgacagca ccctgcaggg cgcgggcggc gtgcgggtcg agcgcggcgc caatgtcacg 660
gtccaacgca gcaccatcgt tgacgggggc ttgcatatcg gcaccctgca gccgctgcag 720
ccggaagacc ttccgcccag ccgggtggtg ctgggcgaca ccagcgtgac cgccgtgccc 780
gccagcggcg cgcccgcggc ggtgtctgta ttcggggcca atgagcttac ggttgatggc 840
gggcacatca ccgggggcg ggcagcgggg gtggcggcca tggacggggc gatcgtgcat 900
ctgcagcgcg cgacgatacg gcggggggac gcgcctgccg gcggtgcggt tccaggcggt 960
gctgttcccg gcggcttcgg ccccctcctt gacggctggt atggcgtgga tgtatcggat 1020
tccaccgtgg acctcgctca gtcgatcgtc gaggcgccgc agctgggcgc cgcgatccgg 1080
gcgggccgcg gcgccagggt gacggtgtcg ggcggcagct tgtccgcacc gcacggcaat 1140
gtcatcgaga ccggcggcgg cgcgcgtcgc ttcccgcctc cggcctcgcc cctgtcgatc 1200
accttgcagg cgggcgcacg ggcgcagggg agggcgctgc tgtaccgggt cctgccggag 1260
cccgtgaagc tgacgctggc gggcggcgcc caggggcagg gcgacatcgt cgcgacggag 1320
ctgcctccca ttccaggcgc gtcgagcggg ccgctcgacg tggcgctggc cagccaggcc 1380
cgatggacgg gcgctacccg cgcggtcgac tcgctgtcca tcgacaacgc cacctgggtc 1440
atgacggaca actcgaacgt cggcgcgctg cggctggcca gcgacggcag cgtcgatttc 1500
cagcagccgg ccgaagctgg gcggttcaag tgcctgatgg tcgatacgct ggcgggttcg 1560
gggctgttcc gcatgaatgt cttcgcggac ctggggctga gcgacaagct ggtcgtcatg 1620
cgggacgcca gcggccagca caggctgttg gtccgcaaca gcggcagcga gccggccagc 1680
ggcaacacca tgctgctggt gcagacgcca cgaggcagcg cggcgacctt tacccttgcc 1740
aacaaggacg gcaaggtcga tatcggtacc taccgctatc gattggccgc caacggcaat 1800
gggcagtgga gcctggtcgg cgcgaaggcg ccgccggcgc ccaagcccgc gccgcagccc 1860
ggtccccagc ccggtcccca gccgccgcag ccgccgcagc cgccgcagcc gccacagagg 1920
cagccggaag cgccggcgcc gcaaccgccg gcgggcaggg agttgtccgc cgccgccaac 1980
gcggcggtca acacgggtgg ggtgggcctg gccagcacgc tctggtacgc cgaaagcaat 2040

-continued

```
gcgttgtcca agcgcctggg cgagttgcgc ctgaatccgg acgccggcgg cgcttggggc   2100

cgcggcttcg cgcaacgcca gcaactggac aaccgcgccg ggcggcgctt cgaccagaag   2160

gtggccggct tcgagctggg cgccgaccac gcggtggcgg tggccggcgg gcgctggcac   2220

ctgggcgggc tggccggcta tacgcgcggc gaccgcggct ttaccggcga cggcggcggc   2280

cacaccgaca gcgtgcatgt cgggggctat gccacctata tcgccaacag cggtttctac   2340

ctggacgcga cgctgcgcgc cagccgcctc gaaaatgact tcaaggtggc gggcagcgat   2400

gggtacgcgg tcaagggcaa gtaccgcacc catggggtag gcgcctcgct cgaggcgggc   2460

cggcgcttcg cccatgccga cggctggttc ctcgagccgc aggccgagct ggcggtgttc   2520

cgggtcggcg gcggttcgta ccgcgcggcc aatggcctgc gggtgcgcga cgaaggcggc   2580

agctcggtgc tgggtcgcct gggcctggag gtcggcaagc gcatcgaact ggcaggcggc   2640

aggcaggtgc agccatacat caaggccagc gtgctgcagg agttcgacgg cgcgggtacg   2700

gtacgcacca acggcatcgc gcaccgcacc gaactgcgcg gcacgcgcgc cgaactgggc   2760

ctgggcatgg ccgccgcgct gggccgcggc cacagcctgt atgcctcgta cgagtactcc   2820

aagggcccga agctggccat gccgtggacc ttccacgcgg gctaccggta cagctggtaa   2880

agcgagaagg gtccatcccc ccgcgggggga gattttcctg gaggttggcc ggtgccagtc   2940

tccaggctca ggcggccagg gcgtgcgggc cgggcaggcc gtgctggtgc tggccgaacc   3000
```

<210> SEQ ID NO 2
<211> LENGTH: 2733
<212> TYPE: DNA
<213> ORGANISM: Bordetella pertussis

<400> SEQUENCE: 2

```
atgaacatgt ctctgtcacg cattgtcaag gcggcgcccc tgcgccgcac cacgctggcc     60

atggcgctgg gcgcgctggg cgccgccccg gcggcgcatg ccgactggaa caaccagtcc    120

atcgtcaaga ccggtgagcg ccagcatggc atccatatcc agggctccga cccgggcggc    180

gtacggaccg ccagcggaac caccatcaag gtaagcggcc gtcaggccca gggcatcctg    240

ctagaaaatc ccgcggccga gctgcagttc cggaacggca gtgtcacgtc gtcgggacag    300

ttgtccgacg atggcatccg gcgctttctg ggcaccgtca ccgtcaaggc cggcaagctg    360

gtcgccgatc acgccacgct ggccaacgtt ggcgacacct gggacgacga cggcatcgcg    420

ctctatgtgg ccggcgaaca ggcccaggcc agcatcgccg acagcaccct gcagggcgct    480

ggcggcgtgc agatcgagcg cggcgccaat gtcacggtcc aacgcagcgc catcgtcgac    540

gggggcttgc atatcggcgc cctgcagtca ttgcagccgg aagaccttcc gcccagccgg    600

gtggtgctgc gcgacaccaa cgtgaccgcc gtgcccgcca gcggcgcgcc cgcggcggtg    660

tctgtgttgg gggccagtga gcttacgctc gacggcgggc acatcaccgg cgggcgggca    720

gcgggggtgg cggccatgca agggggcggtc gtgcatctgc agcgcgcgac gatacggcgc    780

ggggacgcgc ctgccggcgg tgcggttccc ggcggtgcgg ttcccggtgg tgcggttccc    840

ggcggcttcg gtcccggcgg cttcggtccc gtcctcgacg gctggtatgg cgtggacgta    900

tcgggctcca gcgtggagct cgcccagtcg atcgtcgagg cgccggagct gggcgccgca    960

atccgggtgg gccgcggcgc cagggtgacg gtgtcgggcg gcagcttgtc cgcaccgcac   1020

ggcaatgtca tcgagaccgg cggcgcgcgt cgctttgcgc ctcaagccgc gcccctgtcg   1080

atcaccttgc aggccggcgc gcatgcccag gggaaagcgc tgctgtaccg ggtcctgccg   1140
```

-continued

```
gagcccgtga agctgacgct gaccgggggc gccgatgcgc agggcgacat cgtcgcgacg   1200
gagctgccct ccattcccgg cacgtcgatc gggccgctcg acgtggcgct ggccagccag   1260
gcccgatgga cgggcgctac ccgcgcggtc gactcgctgt ccatcgacaa cgccacctgg   1320
gtcatgacgg acaactcgaa cgtcggtgcg ctacggctgg ccagcgacgg cagcgtcgat   1380
ttccagcagc cggccgaagc tgggcggttc aaggtcctga cggtcaatac gctggcgggt   1440
tcggggctgt tccgcatgaa tgtcttcgcg gacctggggc tgagcgacaa gctggtcgtc   1500
atgcaggacg ccagcggcca gcacaggctg tgggtccgca acagcggcag cgagccggcc   1560
agcgccaaca ccctgctgct ggtgcagacg ccacgaggca gcgcggcgac ctttaccctt   1620
gccaacaagg acggcaaggt cgatatcggt acctatcgct atcgattggc cgccaacggc   1680
aatgggcagt ggagcctggt gggcgcgaag gcgccgccgg cgcccaagcc cgcgccgcag   1740
ccgggtcccc agccgccgca gccgccgcag ccgcagccgg aagcgccggc gccgcaaccg   1800
ccggcgggca gggagttgtc cgccgccgcc aacgcggcgg tcaacacggg tggggtgggc   1860
ctggccagca cgctctggta cgccgaaagc aatgcgttgt ccaagcgcct gggcgagttg   1920
cgcctgaatc cggacgccgg cggcgcctgg ggccgcggct tcgcgcaacg ccagcagctg   1980
gacaaccgcg ccgggcggcg cttcgaccag aaggtggccg gcttcgagct gggcgccgac   2040
cacgcggtgg cggtggccgg cggacgctgg cacctgggcg ggctggccgg ctatacgcgc   2100
ggcgaccgcg gcttcaccgg cgacggcggc ggccacaccg acagcgtgca tgtcgggggc   2160
tatgccacat atatcgccga cagcggtttc tacctggacg cgacgctgcg cgccagccgc   2220
ctggagaatg acttcaaggt ggcgggcagc gacgggtacg cggtcaaggg caagtaccgc   2280
acccatgggg tgggcgcctc gctcgaggcg ggccggcgct ttacccatgc cgacggctgg   2340
ttcctcgagc cgcaggccga gctggcggta ttccgggccg gcggcggtgc gtaccgcgcg   2400
gccaacggcc tgcgggtgcg cgacgaaggc ggcagctcgg tgctgggtcg cctgggcctg   2460
gaggtcggca agcgcatcga actggcaggc ggcaggcagg tgcagccata catcaaggcc   2520
agcgtgctgc aggagttcga cggcgcgggt acggtacaca ccaacggcat cgcgcaccgc   2580
accgaactgc gcggcacgcg cgccgaactg ggcctgggca tggccgccgc gctgggccgc   2640
ggccacagcc tgtatgcctc gtacgagtac tccaagggcc cgaagctggc catgccgtgg   2700
accttccacg cgggctaccg gtacagctgg taa                                2733
```

<210> SEQ ID NO 3
<211> LENGTH: 3116
<212> TYPE: DNA
<213> ORGANISM: Bordetella parapertussis

<400> SEQUENCE: 3

```
atcgatgatg cgtcgctgta acacggcaaa taccgtgcat tgcagcggtt ctggatggcg     60
ttcttcgtac gtttgctgcg cccattcttc cctgttccat cgcggtgcgg gcatggcggg    120
cgtctgctct tcacccggca tccaatgaac atgtctctgt cacgcattgt caaggcggcg    180
cccctgcgcc gcaccacact ggccatggcg ctgggcgcgc tgggcgccgc gcccgccgcg    240
tacgccgact ggaacaacca gtccatcatc aaggccggcg agcgccagca cggcatccac    300
atcaagcaaa gcgatggcgc cggcgtacgg accgccaccg gaacgaccat caaggtaagc    360
ggtcgtcagg cccagggcgt cctgctggaa aatcccgcgg ccgagctgcg gttccagaac    420
ggcagcgtca cgtcttcggg acagctgttc gacgaaggcg tccggcgctt tctgggcacc    480
gtcaccgtca aggccggcaa gctggtcgcc gatcacgcca cgctggccaa cgtcagcgac    540
```

-continued

```
acccgggacg acgacggcat cgcgctctat gtggccggcg agcaggccca ggccagcatc    600
gccgacagca ccctgcaggg cgcgggcggc gtgcgggtcg agcgcggcgc caatgtcacg    660
gtccaacgca gcaccatcgt tgacgggggc ttgcatatcg gcaccctgca gccgctgcag    720
ccggaagacc ttccgcccag ccgggtggtg ctgggcgaca ccagcgtgac cgccgtgccc    780
gccagcggcg cgcccgcggc ggtgtttgta ttcggggcca atgagcttac ggttgatggc    840
gggcacatca ccgggggcg ggcagcgggg gtggcggcca tggacggggc gatcgtgcat    900
ctgcagcgcg cgacgatacg gcgggggac gcgcctgccg gcggtgcggt tccaggcggt    960
gcggttcccg gcggtgccgt tcccggcggc ttcggccccc tccttgacgg ctggtatggc   1020
gtggatgtat cggactccac cgtggacctc gctcagtcga tcgtcgaggc gccgcagctg   1080
ggcgccgcga tccgggcggg ccgcggcgcc agggtgacgg tgtcgggcgg cagcttgtcc   1140
gcaccgcacg gcaatgtcat cgagaccggc ggcggtgcgc gtcgcttccc gcctccggcc   1200
tcgcccctgt cgatcacctt gcaggcgggc gcacgggcgc aggggagggc gctgctgtac   1260
cgggtcctgc cggagcccgt gaagctgacg ctggcgggcg gcgcccaggg gcagggcgac   1320
atcgtcgcga cggagctgcc tcccattcca ggcgcgtcga gcgggccgct cgacgtggcg   1380
ctggccagcc aggcccgatg gacgggcgct acccgcgcgg tcgactcgct gtccatcgac   1440
aacgccacct gggtcatgac ggacaactcg aacgtcggcg cgctgcggct ggccagcgac   1500
ggcagcgtcg atttccagca gccggccgaa gctgggcggt tcaaggtcct gatggtcgat   1560
acgctggcgg gttcggggct gttccgcatg aatgtcttcg cggacctggg gctgagcgac   1620
aagctggtcg tcatgcggga cgccagcggc cagcacaggc tgtgggtccg caacagcggc   1680
agcgagccgg ccagcggcaa caccatgctg ctggtgcaga cgccacgagg cagcgcggcg   1740
acctttaccc ttgccaacaa ggacggcaag gtcgatatcg gtacctaccg ctatcgattg   1800
gccgccaacg gcaatgggca gtggagcctg gtgggcgcga aggcgccgcc ggcgcccaag   1860
cccgcgccgc agcccggtcc ccagcccggt ccccagccgc cgcagccgcc gcagccgccg   1920
cagccgccgc agccgccgca gccgccacag aggcagccgg aagcgccggc gccgcaaccg   1980
ccggcgggca gggagttgtc cgccgccgcc aacgcggcgg tcaacacggg tggggtgggc   2040
ctggccagca cgctctggta cgccgaaagc aatgcgttgt ccaagcgcct gggcgagttg   2100
cgcctgaatc cggacgccgg cggcgcttgg ggccgcggct tcgcgcaacg ccagcaactg   2160
gacaaccgcg ccgggcggcg cttcgaccag aaggtggccg gcttcgagct gggcgccgac   2220
cacgcggtgg cggtggccgg cgggcgctgg cacctgggcg ggctggccgg ctatacgcgc   2280
ggcgaccgcg gctttaccgg cgacggcggc ggccacaccg acagcgtgca tgtcgggggc   2340
tatgccacct atatcgccaa cagcggtttc tacctggacg cgacgctgcg cgccagccgc   2400
ctcgaaaatg acttcaaggt ggcgggcagc gatgggtacg cggtcaaggg caagtaccgc   2460
acccatgggg taggcgtctc gctcgaggcg ggccggcgct tcgcccatgc cgacggctgg   2520
ttcctcgagc cgcaggccga gctggcggtg ttccgggtcg gcggcggtgc gtaccgcgcg   2580
gccaatggcc tgcgggtgcg cgacgaaggc ggcagctcgg tgctgggtcg cctgggcctg   2640
gaggtcggca agcgcatcga actggcaggc ggcaggcagg tgcagccata catcaaggcc   2700
agcgtgttgc aggagttcga cggcgcgggt acggtacgca ccaacggcat cgcgcatcgc   2760
accgaactgc gcggcacgcg cgccgaactg ggcctgggca tggccgccgc gctgggccgc   2820
ggccacagcc tgtatgcctc gtacgagtac tccaagggcc cgaagctggc catgccgtgg   2880
```

-continued

```
accttccacg cgggctaccg gtacagctgg taaagcgaga agggtccatc ccccgcggag   2940

gagtttttcc tggaggttgg ccggtgccag tctccaggct caggcggcca gggcctgcgg   3000

gccgggcagg ccgtgctggt gctggccgaa ccattgcaca gggtgttcgg ccaagggcgg   3060

cgacttcgcc gatgaccagc aacgccgggg ggcgcacgct gcgccggcgc gcgatc       3116


<210> SEQ ID NO 4
<211> LENGTH: 911
<212> TYPE: PRT
<213> ORGANISM: Bordetella bronchiseptica

<400> SEQUENCE: 4

Met Asn Met Ser Leu Ser Arg Ile Val Leu Ala Ala Pro Leu Arg Arg
  1               5                  10                  15

Thr Thr Leu Ala Met Ala Leu Gly Ala Leu Gly Ala Ala Pro Ala Ala
             20                  25                  30

Tyr Ala Asp Trp Asn Asn Gln Ser Ile Ile Lys Ala Gly Glu Arg Gln
         35                  40                  45

His Gly Ile His Ile Lys Gln Ser Asp Gly Ala Gly Val Arg Thr Ala
     50                  55                  60

Thr Gly Thr Thr Ile Lys Val Ser Gly Arg Gln Ala Gln Gly Val Leu
 65                  70                  75                  80

Leu Glu Asn Pro Ala Ala Glu Leu Arg Phe Gln Asn Gly Ser Val Thr
                 85                  90                  95

Ser Ser Gly Gln Leu Phe Asp Glu Gly Val Arg Arg Phe Leu Gly Thr
            100                 105                 110

Val Thr Val Lys Ala Gly Lys Leu Val Ala Asp His Ala Thr Leu Ala
        115                 120                 125

Asn Val Ser Asp Thr Arg Asp Asp Asp Gly Ile Ala Leu Tyr Val Ala
    130                 135                 140

Gly Glu Gln Ala Gln Ala Ser Ile Ala Asp Ser Thr Leu Gln Gly Ala
145                 150                 155                 160

Gly Gly Val Arg Val Glu Arg Gly Ala Asn Val Thr Val Gln Arg Ser
                165                 170                 175

Thr Ile Val Asp Gly Gly Leu His Ile Gly Thr Leu Gln Pro Leu Gln
            180                 185                 190

Pro Glu Asp Leu Pro Pro Ser Arg Val Val Leu Gly Asp Thr Ser Val
        195                 200                 205

Thr Ala Val Pro Ala Ser Gly Ala Pro Ala Ala Val Ser Val Phe Gly
    210                 215                 220

Ala Asn Glu Leu Thr Val Asp Gly Gly His Ile Thr Gly Gly Arg Ala
225                 230                 235                 240

Ala Gly Val Ala Ala Met Asp Gly Ala Ile Val His Leu Gln Arg Ala
                245                 250                 255

Thr Ile Arg Arg Gly Asp Ala Pro Ala Gly Gly Ala Val Pro Gly Gly
            260                 265                 270

Ala Val Pro Gly Gly Phe Gly Pro Leu Leu Asp Gly Trp Tyr Gly Val
        275                 280                 285

Asp Val Ser Asp Ser Thr Val Asp Leu Ala Gln Ser Ile Val Glu Ala
    290                 295                 300

Pro Gln Leu Gly Ala Ala Ile Arg Ala Gly Arg Gly Ala Arg Val Thr
305                 310                 315                 320

Val Ser Gly Gly Ser Leu Ser Ala Pro His Gly Asn Val Ile Glu Thr
                325                 330                 335
```

-continued

```
Gly Gly Gly Ala Arg Arg Phe Pro Pro Pro Ala Ser Pro Leu Ser Ile
            340                 345                 350

Thr Leu Gln Ala Gly Ala Arg Ala Gln Gly Arg Ala Leu Leu Tyr Arg
        355                 360                 365

Val Leu Pro Glu Pro Val Lys Leu Thr Leu Ala Gly Gly Ala Gln Gly
    370                 375                 380

Gln Gly Asp Ile Val Ala Thr Glu Leu Pro Pro Ile Pro Gly Ala Ser
385                 390                 395                 400

Ser Gly Pro Leu Asp Val Ala Leu Ala Ser Gln Ala Arg Trp Thr Gly
                405                 410                 415

Ala Thr Arg Ala Val Asp Ser Leu Ser Ile Asp Asn Ala Thr Trp Val
            420                 425                 430

Met Thr Asp Asn Ser Asn Val Gly Ala Leu Arg Leu Ala Ser Asp Gly
        435                 440                 445

Ser Val Asp Phe Gln Gln Pro Ala Glu Ala Gly Arg Phe Lys Cys Leu
    450                 455                 460

Met Val Asp Thr Leu Ala Gly Ser Gly Leu Phe Arg Met Asn Val Phe
465                 470                 475                 480

Ala Asp Leu Gly Leu Ser Asp Lys Leu Val Val Met Arg Asp Ala Ser
                485                 490                 495

Gly Gln His Arg Leu Leu Val Arg Asn Ser Gly Ser Glu Pro Ala Ser
            500                 505                 510

Gly Asn Thr Met Leu Leu Val Gln Thr Pro Arg Gly Ser Ala Ala Thr
        515                 520                 525

Phe Thr Leu Ala Asn Lys Asp Gly Lys Val Asp Ile Gly Thr Tyr Arg
    530                 535                 540

Tyr Arg Leu Ala Ala Asn Gly Asn Gly Gln Trp Ser Leu Val Gly Ala
545                 550                 555                 560

Lys Ala Pro Pro Ala Pro Lys Pro Ala Pro Gln Pro Gly Pro Gln Pro
                565                 570                 575

Gly Pro Gln Pro Pro Gln Pro Pro Gln Pro Pro Gln Pro Pro Gln Arg
            580                 585                 590

Gln Pro Glu Ala Pro Ala Pro Gln Pro Pro Ala Gly Arg Glu Leu Ser
        595                 600                 605

Ala Ala Ala Asn Ala Ala Val Asn Thr Gly Gly Val Gly Leu Ala Ser
    610                 615                 620

Thr Leu Trp Tyr Ala Glu Ser Asn Ala Leu Ser Lys Arg Leu Gly Glu
625                 630                 635                 640

Leu Arg Leu Asn Pro Asp Ala Gly Gly Ala Trp Gly Arg Gly Phe Ala
                645                 650                 655

Gln Arg Gln Gln Leu Asp Asn Arg Ala Gly Arg Arg Phe Asp Gln Lys
            660                 665                 670

Val Ala Gly Phe Glu Leu Gly Ala Asp His Ala Val Ala Val Ala Gly
        675                 680                 685

Gly Arg Trp His Leu Gly Gly Leu Ala Gly Tyr Thr Arg Gly Asp Arg
    690                 695                 700

Gly Phe Thr Gly Asp Gly Gly Gly His Thr Asp Ser Val His Val Gly
705                 710                 715                 720

Gly Tyr Ala Thr Tyr Ile Ala Asn Ser Gly Phe Tyr Leu Asp Ala Thr
                725                 730                 735

Leu Arg Ala Ser Arg Leu Glu Asn Asp Phe Lys Val Ala Gly Ser Asp
            740                 745                 750

Gly Tyr Ala Val Lys Gly Lys Tyr Arg Thr His Gly Val Gly Ala Ser
```

-continued

```
        755                 760                 765

Leu Glu Ala Gly Arg Arg Phe Ala His Ala Asp Gly Trp Phe Leu Glu
    770                 775                 780

Pro Gln Ala Glu Leu Ala Val Phe Arg Val Gly Gly Gly Ser Tyr Arg
785                 790                 795                 800

Ala Ala Asn Gly Leu Arg Val Arg Asp Glu Gly Gly Ser Ser Val Leu
                805                 810                 815

Gly Arg Leu Gly Leu Glu Val Gly Lys Arg Ile Glu Leu Ala Gly Gly
            820                 825                 830

Arg Gln Val Gln Pro Tyr Ile Lys Ala Ser Val Leu Gln Glu Phe Asp
        835                 840                 845

Gly Ala Gly Thr Val Arg Thr Asn Gly Ile Ala His Arg Thr Glu Leu
    850                 855                 860

Arg Gly Thr Arg Ala Glu Leu Gly Leu Gly Met Ala Ala Ala Leu Gly
865                 870                 875                 880

Arg Gly His Ser Leu Tyr Ala Ser Tyr Glu Tyr Ser Lys Gly Pro Lys
                885                 890                 895

Leu Ala Met Pro Trp Thr Phe His Ala Gly Tyr Arg Tyr Ser Trp
            900                 905                 910


<210> SEQ ID NO 5
<211> LENGTH: 910
<212> TYPE: PRT
<213> ORGANISM: Bordetella pertussis

<400> SEQUENCE: 5

Met Asn Met Ser Leu Ser Arg Ile Val Lys Ala Ala Pro Leu Arg Arg
  1               5                  10                  15

Thr Thr Leu Ala Met Ala Leu Gly Ala Leu Gly Ala Ala Pro Ala Ala
             20                  25                  30

His Ala Asp Trp Asn Asn Gln Ser Ile Val Lys Thr Gly Glu Arg Gln
         35                  40                  45

His Gly Ile His Ile Gln Gly Ser Asp Pro Gly Gly Val Arg Thr Ala
     50                  55                  60

Ser Gly Thr Thr Ile Lys Val Ser Gly Arg Gln Ala Gln Gly Ile Leu
 65                  70                  75                  80

Leu Glu Asn Pro Ala Ala Glu Leu Gln Phe Arg Asn Gly Ser Val Thr
                 85                  90                  95

Ser Ser Gly Gln Leu Ser Asp Asp Gly Ile Arg Arg Phe Leu Gly Thr
            100                 105                 110

Val Thr Val Lys Ala Gly Lys Leu Val Ala Asp His Ala Thr Leu Ala
        115                 120                 125

Asn Val Gly Asp Thr Trp Asp Asp Asp Gly Ile Ala Leu Tyr Val Ala
    130                 135                 140

Gly Glu Gln Ala Gln Ala Ser Ile Ala Asp Ser Thr Leu Gln Gly Ala
145                 150                 155                 160

Gly Gly Val Gln Ile Glu Arg Gly Ala Asn Val Thr Val Gln Arg Ser
                165                 170                 175

Ala Ile Val Asp Gly Gly Leu His Ile Gly Ala Leu Gln Ser Leu Gln
            180                 185                 190

Pro Glu Asp Leu Pro Pro Ser Arg Val Val Leu Arg Asp Thr Asn Val
        195                 200                 205

Thr Ala Val Pro Ala Ser Gly Ala Pro Ala Ala Val Ser Val Leu Gly
    210                 215                 220
```

-continued

```
Ala Ser Glu Leu Thr Leu Asp Gly Gly His Ile Thr Gly Gly Arg Ala
225                 230                 235                 240

Ala Gly Val Ala Ala Met Gln Gly Ala Val Val His Leu Gln Arg Ala
                245                 250                 255

Thr Ile Arg Arg Gly Asp Ala Pro Ala Gly Gly Ala Val Pro Gly Gly
            260                 265                 270

Ala Val Pro Gly Gly Ala Val Pro Gly Gly Phe Gly Pro Gly Gly Phe
        275                 280                 285

Gly Pro Val Leu Asp Gly Trp Tyr Gly Val Asp Val Ser Asp Ser Ser
    290                 295                 300

Val Glu Leu Ala Gln Ser Ile Val Glu Ala Pro Glu Leu Gly Ala Ala
305                 310                 315                 320

Ile Arg Val Gly Arg Gly Ala Arg Val Thr Val Ser Gly Gly Ser Leu
                325                 330                 335

Ser Ala Pro His Gly Asn Val Ile Glu Thr Gly Gly Ala Arg Arg Phe
            340                 345                 350

Ala Pro Gln Ala Ala Pro Leu Ser Ile Thr Leu Gln Ala Gly Ala His
        355                 360                 365

Ala Gln Gly Lys Ala Leu Leu Tyr Arg Val Leu Pro Glu Pro Val Lys
    370                 375                 380

Leu Thr Leu Thr Gly Gly Ala Asp Ala Gln Gly Asp Ile Val Ala Thr
385                 390                 395                 400

Glu Leu Pro Ser Ile Pro Gly Thr Ser Ile Gly Pro Leu Asp Val Ala
                405                 410                 415

Leu Ala Ser Gln Ala Arg Trp Thr Gly Ala Thr Arg Ala Val Asp Ser
            420                 425                 430

Leu Ser Ile Asp Asn Ala Thr Trp Val Met Thr Asp Asn Ser Asn Val
        435                 440                 445

Gly Ala Leu Arg Leu Ala Ser Asp Gly Ser Val Asp Phe Gln Gln Pro
    450                 455                 460

Ala Glu Ala Gly Arg Phe Lys Val Leu Thr Val Asn Thr Leu Ala Gly
465                 470                 475                 480

Ser Gly Leu Phe Arg Met Asn Val Phe Ala Asp Leu Gly Leu Ser Asp
                485                 490                 495

Lys Leu Val Val Met Gln Asp Ala Ser Gly Gln His Arg Leu Trp Val
            500                 505                 510

Arg Asn Ser Gly Ser Glu Pro Ala Ser Ala Asn Thr Leu Leu Leu Val
        515                 520                 525

Gln Thr Pro Arg Gly Ser Ala Ala Thr Phe Thr Leu Ala Asn Lys Asp
    530                 535                 540

Gly Lys Val Asp Ile Gly Thr Tyr Arg Tyr Arg Leu Ala Ala Asn Gly
545                 550                 555                 560

Asn Gly Gln Trp Ser Leu Val Gly Ala Lys Ala Pro Pro Ala Pro Lys
                565                 570                 575

Pro Ala Pro Gln Pro Gly Pro Gln Pro Pro Gln Pro Pro Gln Pro Gln
            580                 585                 590

Pro Glu Ala Pro Ala Pro Gln Pro Pro Ala Gly Arg Glu Leu Ser Ala
        595                 600                 605

Ala Ala Asn Ala Ala Val Asn Thr Gly Gly Val Gly Leu Ala Ser Thr
    610                 615                 620

Leu Trp Tyr Ala Glu Ser Asn Ala Leu Ser Lys Arg Leu Gly Glu Leu
625                 630                 635                 640

Arg Leu Asn Pro Asp Ala Gly Gly Ala Trp Gly Arg Gly Phe Ala Gln
```

-continued

```
                645                 650                 655

Arg Gln Gln Leu Asp Asn Arg Ala Gly Arg Arg Phe Asp Gln Lys Val
            660                 665                 670

Ala Gly Phe Glu Leu Gly Ala Asp His Ala Val Ala Val Ala Gly Gly
        675                 680                 685

Arg Trp His Leu Gly Gly Leu Ala Gly Tyr Thr Arg Gly Asp Arg Gly
    690                 695                 700

Phe Thr Gly Asp Gly Gly Gly His Thr Asp Ser Val His Val Gly Gly
705                 710                 715                 720

Tyr Ala Thr Tyr Ile Ala Asp Ser Gly Phe Tyr Leu Asp Ala Thr Leu
                725                 730                 735

Arg Ala Ser Arg Leu Glu Asn Asp Phe Lys Val Ala Gly Ser Asp Gly
            740                 745                 750

Tyr Ala Val Lys Gly Lys Tyr Arg Thr His Gly Val Gly Ala Ser Leu
        755                 760                 765

Glu Ala Gly Arg Arg Phe Thr His Ala Asp Gly Trp Phe Leu Glu Pro
    770                 775                 780

Gln Ala Glu Leu Ala Val Phe Arg Ala Gly Gly Gly Ala Tyr Arg Ala
785                 790                 795                 800

Ala Asn Gly Leu Arg Val Arg Asp Glu Gly Gly Ser Ser Val Leu Gly
                805                 810                 815

Arg Leu Gly Leu Glu Val Gly Lys Arg Ile Glu Leu Ala Gly Gly Arg
            820                 825                 830

Gln Val Gln Pro Tyr Ile Lys Ala Ser Val Leu Gln Glu Phe Asp Gly
        835                 840                 845

Ala Gly Thr Val His Thr Asn Gly Ile Ala His Arg Thr Glu Leu Arg
    850                 855                 860

Gly Thr Arg Ala Glu Leu Gly Leu Gly Met Ala Ala Ala Leu Gly Arg
865                 870                 875                 880

Gly His Ser Leu Tyr Ala Ser Tyr Glu Tyr Ser Lys Gly Pro Lys Leu
                885                 890                 895

Ala Met Pro Trp Thr Phe His Ala Gly Tyr Arg Tyr Ser Trp
            900                 905                 910


<210> SEQ ID NO 6
<211> LENGTH: 922
<212> TYPE: PRT
<213> ORGANISM: Bordetella parapertussis

<400> SEQUENCE: 6

Met Asn Met Ser Leu Ser Arg Ile Val Lys Ala Ala Pro Leu Arg Arg
  1               5                  10                  15

Thr Thr Leu Ala Met Ala Leu Gly Ala Leu Gly Ala Ala Pro Ala Ala
             20                  25                  30

Tyr Ala Asp Trp Asn Asn Gln Ser Ile Ile Lys Ala Gly Glu Arg Gln
         35                  40                  45

His Gly Ile His Ile Lys Gln Ser Asp Gly Ala Gly Val Arg Thr Ala
     50                  55                  60

Thr Gly Thr Thr Ile Lys Val Ser Gly Arg Gln Ala Gln Gly Val Leu
 65                  70                  75                  80

Leu Glu Asn Pro Ala Ala Glu Leu Arg Phe Gln Asn Gly Ser Val Thr
                 85                  90                  95

Ser Ser Gly Gln Leu Phe Asp Glu Gly Val Arg Arg Phe Leu Gly Thr
            100                 105                 110
```

-continued

```
Val Thr Val Lys Ala Gly Lys Leu Val Ala Asp His Ala Thr Leu Ala
        115                 120                 125

Asn Val Ser Asp Thr Arg Asp Asp Asp Gly Ile Ala Leu Tyr Val Ala
    130                 135                 140

Gly Glu Gln Ala Gln Ala Ser Ile Ala Asp Ser Thr Leu Gln Gly Ala
145                 150                 155                 160

Gly Gly Val Arg Val Glu Arg Gly Ala Asn Val Thr Val Gln Arg Ser
                165                 170                 175

Thr Ile Val Asp Gly Gly Leu His Ile Gly Thr Leu Gln Pro Leu Gln
            180                 185                 190

Pro Glu Asp Leu Pro Pro Ser Arg Val Val Leu Gly Asp Thr Ser Val
        195                 200                 205

Thr Ala Val Pro Ala Ser Gly Ala Pro Ala Ala Val Phe Val Phe Gly
    210                 215                 220

Ala Asn Glu Leu Thr Val Asp Gly Gly His Ile Thr Gly Gly Arg Ala
225                 230                 235                 240

Ala Gly Val Ala Ala Met Asp Gly Ala Ile Val His Leu Gln Arg Ala
                245                 250                 255

Thr Ile Arg Arg Gly Asp Ala Pro Ala Gly Gly Ala Val Pro Gly Gly
            260                 265                 270

Ala Val Pro Gly Gly Ala Val Pro Gly Gly Phe Gly Pro Leu Leu Asp
        275                 280                 285

Gly Trp Tyr Gly Val Asp Val Ser Asp Ser Thr Val Asp Leu Ala Gln
    290                 295                 300

Ser Ile Val Glu Ala Pro Gln Leu Gly Ala Ala Ile Arg Ala Gly Arg
305                 310                 315                 320

Gly Ala Arg Val Thr Val Ser Gly Gly Ser Leu Ser Ala Pro His Gly
                325                 330                 335

Asn Val Ile Glu Thr Gly Gly Gly Ala Arg Arg Phe Pro Pro Pro Ala
            340                 345                 350

Ser Pro Leu Ser Ile Thr Leu Gln Ala Gly Ala Arg Ala Gln Gly Arg
        355                 360                 365

Ala Leu Leu Tyr Arg Val Leu Pro Glu Pro Val Lys Leu Thr Leu Ala
    370                 375                 380

Gly Gly Ala Gln Gly Gln Gly Asp Ile Val Ala Thr Glu Leu Pro Pro
385                 390                 395                 400

Ile Pro Gly Ala Ser Ser Gly Pro Leu Asp Val Ala Leu Ala Ser Gln
                405                 410                 415

Ala Arg Trp Thr Gly Ala Thr Arg Ala Val Asp Ser Leu Ser Ile Asp
            420                 425                 430

Asn Ala Thr Trp Val Met Thr Asp Asn Ser Asn Val Gly Ala Leu Arg
        435                 440                 445

Leu Ala Ser Asp Gly Ser Val Asp Phe Gln Gln Pro Ala Glu Ala Gly
    450                 455                 460

Arg Phe Lys Val Leu Met Val Asp Thr Leu Ala Gly Ser Gly Leu Phe
465                 470                 475                 480

Arg Met Asn Val Phe Ala Asp Leu Gly Leu Ser Asp Lys Leu Val Val
                485                 490                 495

Met Arg Asp Ala Ser Gly Gln His Arg Leu Trp Val Arg Asn Ser Gly
            500                 505                 510

Ser Glu Pro Ala Ser Gly Asn Thr Met Leu Leu Val Gln Thr Pro Arg
        515                 520                 525

Gly Ser Ala Ala Thr Phe Thr Leu Ala Asn Lys Asp Gly Lys Val Asp
```

-continued

```
    530                 535                 540

Ile Gly Thr Tyr Arg Tyr Arg Leu Ala Ala Asn Gly Asn Gly Gln Trp
545                 550                 555                 560

Ser Leu Val Gly Ala Lys Ala Pro Pro Ala Pro Lys Pro Ala Pro Gln
                565                 570                 575

Pro Gly Pro Gln Pro Gly Pro Gln Pro Pro Gln Pro Pro Gln Pro Pro
            580                 585                 590

Gln Pro Pro Gln Pro Pro Gln Pro Pro Gln Arg Gln Pro Glu Ala Pro
        595                 600                 605

Ala Pro Gln Pro Pro Ala Gly Arg Glu Leu Ser Ala Ala Ala Asn Ala
    610                 615                 620

Ala Val Asn Thr Gly Gly Val Gly Leu Ala Ser Thr Leu Trp Tyr Ala
625                 630                 635                 640

Glu Ser Asn Ala Leu Ser Lys Arg Leu Gly Glu Leu Arg Leu Asn Pro
                645                 650                 655

Asp Ala Gly Gly Ala Trp Gly Arg Gly Phe Ala Gln Arg Gln Gln Leu
            660                 665                 670

Asp Asn Arg Ala Gly Arg Arg Phe Asp Gln Lys Val Ala Gly Phe Glu
        675                 680                 685

Leu Gly Ala Asp His Ala Val Ala Val Ala Gly Gly Arg Trp His Leu
    690                 695                 700

Gly Gly Leu Ala Gly Tyr Thr Arg Gly Asp Arg Gly Phe Thr Gly Asp
705                 710                 715                 720

Gly Gly Gly His Thr Asp Ser Val His Val Gly Gly Tyr Ala Thr Tyr
                725                 730                 735

Ile Ala Asn Ser Gly Phe Tyr Leu Asp Ala Thr Leu Arg Ala Ser Arg
            740                 745                 750

Leu Glu Asn Asp Phe Lys Val Ala Gly Ser Asp Gly Tyr Ala Val Lys
        755                 760                 765

Gly Lys Tyr Arg Thr His Gly Val Gly Val Ser Leu Glu Ala Gly Arg
    770                 775                 780

Arg Phe Ala His Ala Asp Gly Trp Phe Leu Glu Pro Gln Ala Glu Leu
785                 790                 795                 800

Ala Val Phe Arg Val Gly Gly Gly Ala Tyr Arg Ala Ala Asn Gly Leu
                805                 810                 815

Arg Val Arg Asp Glu Gly Gly Ser Ser Val Leu Gly Arg Leu Gly Leu
            820                 825                 830

Glu Val Gly Lys Arg Ile Glu Leu Ala Gly Gly Arg Gln Val Gln Pro
        835                 840                 845

Tyr Ile Lys Ala Ser Val Leu Gln Glu Phe Asp Gly Ala Gly Thr Val
    850                 855                 860

Arg Thr Asn Gly Ile Ala His Arg Thr Glu Leu Arg Gly Thr Arg Ala
865                 870                 875                 880

Glu Leu Gly Leu Gly Met Ala Ala Ala Leu Gly Arg Gly His Ser Leu
                885                 890                 895

Tyr Ala Ser Tyr Glu Tyr Ser Lys Gly Pro Lys Leu Ala Met Pro Trp
            900                 905                 910

Thr Phe His Ala Gly Tyr Arg Tyr Ser Trp
        915                 920
```

<210> SEQ ID NO 7
<211> LENGTH: 51
<212> TYPE: PRT
<213> ORGANISM: Bordetella bronchiseptica -continued

<400> SEQUENCE: 7

```
Gln Arg Ala Thr Ile Arg Arg Gly Asp Ala Pro Ala Gly Gly Ala Val
  1               5                  10                  15

Pro Gly Gly Ala Val Pro Gly Gly Ala Val Pro Gly Gly Phe Gly Pro
             20                  25                  30

Leu Leu Asp Gly Trp Tyr Gly Val Asp Val Ser Asp Ser Thr Val Asp
         35                  40                  45

Leu Ala Gln
     50
```

<210> SEQ ID NO 8
<211> LENGTH: 46
<212> TYPE: PRT
<213> ORGANISM: Bordetella bronchiseptica

<400> SEQUENCE: 8

```
Gln Arg Ala Thr Ile Arg Arg Gly Asp Ala Pro Ala Gly Gly Ala Val
  1               5                  10                  15

Pro Gly Gly Ala Val Pro Gly Gly Phe Gly Pro Leu Leu Asp Gly Trp
             20                  25                  30

Tyr Gly Val Asp Val Ser Asp Ser Thr Val Asp Leu Ala Gln
         35                  40                  45
```

<210> SEQ ID NO 9
<211> LENGTH: 56
<212> TYPE: PRT
<213> ORGANISM: Bordetella bronchiseptica

<400> SEQUENCE: 9

```
Gln Arg Ala Thr Ile Arg Arg Gly Asp Ala Pro Ala Gly Gly Gly Val
  1               5                  10                  15

Pro Gly Gly Ala Val Pro Gly Gly Phe Asp Pro Gly Gly Phe Gly Pro
             20                  25                  30

Gly Gly Phe Gly Pro Val Leu Asp Gly Trp Tyr Gly Val Asp Val Ser
         35                  40                  45

Gly Ser Thr Val Glu Leu Ala Gln
     50                  55
```

<210> SEQ ID NO 10
<211> LENGTH: 56
<212> TYPE: PRT
<213> ORGANISM: Bordetella bronchiseptica

<400> SEQUENCE: 10

```
Gln Arg Ala Thr Ile Arg Arg Gly Asp Ala Pro Ala Gly Gly Ala Val
  1               5                  10                  15

Pro Gly Gly Ala Val Pro Gly Gly Ala Val Pro Gly Gly Phe Gly Pro
             20                  25                  30

Gly Gly Phe Gly Pro Val Leu Asp Gly Trp Tyr Gly Val Asp Val Ser
         35                  40                  45

Gly Ser Ser Val Glu Leu Ala Gln
     50                  55
```

<210> SEQ ID NO 11
<211> LENGTH: 61
<212> TYPE: PRT
<213> ORGANISM: Bordetella bronchiseptica

<400> SEQUENCE: 11

-continued

```
Gln Arg Ala Thr Ile Arg Arg Gly Asp Ala Pro Ala Gly Gly Ala Val
  1               5                  10                  15

Pro Gly Gly Ala Val Pro Gly Gly Phe Gly Pro Gly Gly Phe Gly Pro
             20                  25                  30

Gly Gly Phe Gly Pro Gly Gly Phe Gly Pro Val Leu Asp Gly Trp Tyr
         35                  40                  45

Gly Val Asp Val Ser Gly Ser Ser Val Glu Leu Ala Gln
     50                  55                  60


<210> SEQ ID NO 12
<211> LENGTH: 56
<212> TYPE: PRT
<213> ORGANISM: Bordetella bronchiseptica

<400> SEQUENCE: 12

Gln Arg Ala Thr Ile Arg Arg Gly Asp Ala Pro Ala Gly Gly Ala Val
  1               5                  10                  15

Pro Gly Gly Ala Val Pro Gly Gly Phe Gly Pro Gly Gly Phe Gly Pro
             20                  25                  30

Gly Gly Phe Gly Pro Val Leu Asp Gly Trp Tyr Gly Val Asp Val Ser
         35                  40                  45

Gly Ser Ser Val Glu Leu Ala Gln
     50                  55


<210> SEQ ID NO 13
<211> LENGTH: 51
<212> TYPE: PRT
<213> ORGANISM: Bordetella bronchiseptica

<400> SEQUENCE: 13

Gln Arg Ala Thr Ile Arg Arg Gly Asp Ala Pro Ala Gly Gly Ala Val
  1               5                  10                  15

Pro Gly Gly Ala Val Pro Gly Gly Phe Gly Pro Gly Gly Phe Gly Pro
             20                  25                  30

Val Leu Asp Gly Trp Tyr Gly Val Asp Val Ser Gly Ser Ser Val Glu
         35                  40                  45

Leu Ala Gln
     50


<210> SEQ ID NO 14
<211> LENGTH: 49
<212> TYPE: PRT
<213> ORGANISM: Bordetella bronchiseptica

<400> SEQUENCE: 14

Gly Ala Lys Ala Pro Pro Ala Pro Lys Pro Ala Pro Gln Pro Gly Pro
  1               5                  10                  15

Gln Pro Gly Pro Gln Pro Pro Gln Pro Pro Gln Pro Pro Gln Arg Gln
             20                  25                  30

Pro Glu Ala Pro Ala Pro Gln Pro Pro Ala Gly Arg Glu Leu Ser Ala
         35                  40                  45

Ala


<210> SEQ ID NO 15
<211> LENGTH: 52
<212> TYPE: PRT
<213> ORGANISM: Bordetella bronchiseptica

<400> SEQUENCE: 15
```

-continued

```
Gly Ala Lys Ala Pro Pro Ala Pro Lys Pro Ala Pro Gln Pro Gly Pro
  1               5                  10                  15

Gln Pro Gly Pro Gln Pro Pro Gln Pro Pro Gln Pro Pro Gln Pro Pro
             20                  25                  30

Gln Arg Gln Pro Glu Ala Pro Ala Pro Gln Pro Pro Ala Gly Arg Glu
         35                  40                  45

Leu Ser Ala Ala
     50


<210> SEQ ID NO 16
<211> LENGTH: 59
<212> TYPE: PRT
<213> ORGANISM: Bordetella bronchiseptica

<400> SEQUENCE: 16

Gly Ala Lys Ala Pro Pro Ala Pro Lys Pro Ala Pro Gln Pro Gly Pro
  1               5                  10                  15

Gln Pro Gly Pro Gln Pro Gly Pro Gln Pro Gly Pro Gln Pro Pro Gln
             20                  25                  30

Pro Pro Gln Pro Pro Gln Pro Pro Gln Arg Pro Glu Ala Pro Ala Pro
         35                  40                  45

Gln Pro Pro Ala Gly Arg Glu Leu Ser Ala Ala
     50                  55


<210> SEQ ID NO 17
<211> LENGTH: 52
<212> TYPE: PRT
<213> ORGANISM: Bordetella bronchiseptica

<400> SEQUENCE: 17

Gly Ala Lys Ala Pro Pro Ala Pro Lys Pro Ala Pro Gln Pro Gly Pro
  1               5                  10                  15

Gln Pro Gly Pro Gln Pro Gly Pro Gln Pro Pro Gln Pro Pro Gln Pro
             20                  25                  30

Pro Gln Arg Pro Glu Ala Pro Ala Pro Gln Pro Pro Ala Gly Arg Glu
         35                  40                  45

Leu Ser Ala Ala
     50


<210> SEQ ID NO 18
<211> LENGTH: 56
<212> TYPE: PRT
<213> ORGANISM: Bordetella bronchiseptica

<400> SEQUENCE: 18

Gly Ala Lys Ala Pro Pro Ala Pro Lys Pro Ala Pro Gln Pro Gly Pro
  1               5                  10                  15

Gln Pro Gly Pro Gln Pro Gly Pro Gln Pro Pro Gln Pro Pro Gln Pro
             20                  25                  30

Pro Gln Pro Pro Gln Arg Gln Pro Glu Ala Pro Ala Pro Gln Pro Pro
         35                  40                  45

Ala Gly Arg Glu Leu Ser Ala Ala
     50                  55


<210> SEQ ID NO 19
<211> LENGTH: 58
<212> TYPE: PRT
<213> ORGANISM: Bordetella bronchiseptica
```

-continued

<400> SEQUENCE: 19

Gly Ala Lys Ala Pro Pro Ala Pro Lys Pro Ala Pro Gln Pro Gly Pro
1 5 10 15

Gln Pro Gly Pro Gln Pro Pro Gln Pro Pro Gln Pro Pro Gln Pro Pro
20 25 30

Gln Pro Pro Gln Pro Pro Gln Arg Gln Pro Glu Ala Pro Ala Pro Gln
35 40 45

Pro Pro Ala Gly Arg Glu Leu Ser Ala Ala
50 55

<210> SEQ ID NO 20
<211> LENGTH: 48
<212> TYPE: PRT
<213> ORGANISM: Bordetella bronchiseptica

<400> SEQUENCE: 20

Gly Ala Lys Ala Pro Pro Ala Pro Lys Pro Ala Pro Gln Pro Gly Pro
1 5 10 15

Gln Pro Pro Gln Pro Pro Gln Pro Pro Gln Pro Pro Gln Arg Gln Pro
20 25 30

Glu Ala Pro Ala Pro Gln Pro Pro Ala Gly Arg Glu Leu Ser Ala Ala
35 40 45

<210> SEQ ID NO 21
<211> LENGTH: 52
<212> TYPE: PRT
<213> ORGANISM: Bordetella bronchiseptica

<400> SEQUENCE: 21

Gly Ala Lys Val Pro Pro Ala Pro Lys Pro Ala Pro Gln Pro Gly Pro
1 5 10 15

Gln Pro Pro Gln Pro Pro Gln Pro Pro Gln Pro Pro Gln Pro Gln Pro
20 25 30

Gln Pro Gln Pro Glu Ala Pro Ala Pro Gln Pro Pro Ala Gly Arg Glu
35 40 45

Leu Ser Ala Ala
50

<210> SEQ ID NO 22
<211> LENGTH: 54
<212> TYPE: PRT
<213> ORGANISM: Bordetella bronchiseptica

<400> SEQUENCE: 22

Gly Ala Lys Val Pro Pro Ala Pro Lys Pro Ala Pro Gln Pro Gly Pro
1 5 10 15

Gln Pro Pro Gln Pro Pro Gln Pro Pro Gln Pro Pro Gln Pro Gln Pro
20 25 30

Gln Pro Gln Pro Gln Pro Glu Ala Pro Ala Pro Gln Pro Pro Ala Gly
35 40 45

Arg Glu Leu Ser Ala Ala
50

<210> SEQ ID NO 23
<211> LENGTH: 42
<212> TYPE: PRT
<213> ORGANISM: Bordetella bronchiseptica

<400> SEQUENCE: 23

-continued

```
Gly Ala Lys Ala Pro Pro Ala Pro Lys Pro Ala Pro Gln Pro Gly Pro
  1               5                  10                  15

Gln Pro Pro Gln Pro Pro Gln Pro Gln Pro Glu Ala Pro Ala Pro Gln
             20                  25                  30

Pro Pro Ala Gly Arg Glu Leu Ser Ala Ala
         35                  40


<210> SEQ ID NO 24
<211> LENGTH: 39
<212> TYPE: PRT
<213> ORGANISM: Bordetella bronchiseptica

<400> SEQUENCE: 24

Gly Ala Lys Ala Pro Pro Ala Pro Lys Pro Ala Pro Gln Pro Gly Pro
  1               5                  10                  15

Gln Pro Pro Gln Pro Gln Pro Glu Ala Pro Ala Pro Gln Pro Pro Ala
             20                  25                  30

Gly Arg Glu Leu Ser Ala Ala
         35


<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Phe Asp, Phe Gly or Ala Val

<400> SEQUENCE: 25

Gly Gly Xaa Xaa Pro
  1               5
```